(12) United States Patent
Smith et al.

(10) Patent No.: US 8,153,760 B2
(45) Date of Patent: Apr. 10, 2012

(54) RHINOVIRUS VACCINES

(75) Inventors: Thomas J. Smith, Saint Louis, MO (US); Umesh C. Katpally, Saint Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 387 days.

(21) Appl. No.: 11/795,623

(22) PCT Filed: Jan. 17, 2006

(86) PCT No.: PCT/US2006/001588
§ 371 (c)(1), (2), (4) Date: Jul. 19, 2007

(87) PCT Pub. No.: WO2006/078648
PCT Pub. Date: Jul. 27, 2006

(65) Prior Publication Data
US 2009/0202583 A1    Aug. 13, 2009

Related U.S. Application Data

(60) Provisional application No. 60/645,353, filed on Jan. 19, 2005.

(51) Int. Cl.
*C07K 14/95* (2006.01)
*A61K 35/76* (2006.01)

(52) U.S. Cl. .................. 530/324; 424/211.1; 424/93.1

(58) Field of Classification Search .................. None
See application file for complete search history.

(56) References Cited

U.S. PATENT DOCUMENTS
4,215,051 A    7/1980  Palmer

OTHER PUBLICATIONS

Wheeler et al. J. Virol. 1986, vol. 58, No. 2, p. 307-313.*
Katpally et al. Journal of Virology, Jul. 2009, vol. 83, No. 14, pp. 7040-7048.*
Miller-Keane Encyclopedia and Dictionary of Medicine, Nursing, and Allied Health, Seventh Edition. © 2003 by Saunders, an imprint of Elsevier, Inc.*
Ishiko H. for Q80SH7-9PICO, EMBL/GenBank/DDBJ databases, 2002.*
Francis et al. J. Gene Virol. 1987, vol. 68, pp. 2687-2691.*
Bothner, B. et al., (1999) Crystallographically Identical Virus Capsids Display Different Properties in Solution; *Nature Struc. Biol.* 6: 114-116.
Colonno, R.J. et la., (1988) Evidence for the Direct Involvement of the Rhinovirus Canyon in Receptor Binding, *Proc. Natl. Acad. Sci USA* 85: 5449-5453.
Fricks, C.E., et al., (1990) Cell-induced Conformational Change in Poliovirus: Externalization of the Amino Terminus of VP1 is Responsible for Liposome Binding; *J. Virol.* 64: 1934-1945.
Kolatkar, P.R. et al., (1999) Structural Studies of Two Rhinovirus Serotypes Complexed with Fragments of their Cellular Receptor; *EMBO J.* 18: 6249-6259.
Lewis, J.K., e al. (1998) Antiviral Agent Blocks Breathing of the Common Cold Virus,; *Proc. Natl. Acad. Sci* 95: 6774-6778.
Li, Q. et al., (1994) Poliovirus Neutralization by Antibodies to Internal Epitopes of VP4 and VP1 Results from Reversible Exposure of the Sequences at Physiological Temperatures; *J. Virol.* 68: 3965-3970.
Olson, N.H. et al., (1993) Structure of a Human Rhinovirus Complexed with its Receptor Molecule; *Proc. Natl. Acad. Sci.* 90: 507-511.
Sherry, B. et al. (1996) Use of Monoclonal Antibodies to Identify Four Neutralization Immunogens on a Common Cold Picornavirus, Human Rhinovirus 14; *J. Virol.* 57: 246-257.
Sherry, B. et al., (1985) Evidence for at Least Two Dominant Neutralization Antigens on Human Rhinovirus 14; *J. Virol.* 53: 137-143.
Rossman, M.G., et al. (1985) Structure of a Human Common Cold Virus and Functional Relationship to Other Picornaviruses; *Nature* (London) 317: 145-153.
Smith, T.J., et al., (1986) The Site of Attachment in Human Rhinovirus 14 for Antiviral Agents that Inhibit Uncoating; *Science* 233: 1286-1293.
Lee et al (2003) J. Virol. 77 6235-6244.
Bothner et al., (1998) J. Biol. Chem. 273 673-76.
Pulli et al, (1998) Virology 240 202-212.
Jimenez-Clavero et al. (2000) Virology 270 76-83.
Hopp et al., (1981) PNAS 78(6) 3824-28.
Logan & Shenk (1984) PNAS 81 3655-3659.
Koo et al., (1999) PNAS 96 7774-79.
Usha et al., (1993) Virology 197 366-74.
Fitchen et al., (1995) Vaccine 13 1051-57.
McLain et al., (1995) AIDS Res. Hum. Retrovires 11 327-34.
Sugiyama et al., (1995) FEBS Lett. 359 247-250.
Janknecht et al (1991) PNAS 88 8972-76.
Bernatowicz et al. (1986) Anal. Biochem. 155 95-102.
Shepard et al., (1993) J. Cirol. 67 2245-54.

* cited by examiner

*Primary Examiner* — Bao Li
(74) *Attorney, Agent, or Firm* — Dennis A. Bennett; Charles E. Cohen

(57) ABSTRACT

The present invention relates generally to peptide vaccines. More specifically, the present invention relates to vaccines against rhinoviruses and other related and non-related pathogenic animal viruses. In addition, the present invention relates generally to methods of designing and producing vaccines against viruses and, in certain embodiments, against rhinoviruses and other pathogenic viruses.

10 Claims, 10 Drawing Sheets

FIG 1

```
GAQVSTQKSGSHENQNILTNGSHQTFTVINYYKDAASSSSAGQSLSMDPS  (SEQ. ID. NO. 3)
GAQVSTQKSGSHENQNILTNGSHQTFTVINYYKDAASSSSAGQSLSMDPS  (SEQ. ID. NO. 4)
GAQVSTQKSGSHENQNILTNGSHQTFTVINYYKDAASSSSAGQSLSMDPS  (SEQ. ID. NO. 5)
GAQVSTQKSGSHENQNILTNGSNQTFTVINYYKDAASSSSAGQSLSMDPS  (SEQ. ID. NO. 6)
GAQVSTQKSGSHENQNILTNGSNQTFTVINYYKDAASSSSAGQSLSMDPS  (SEQ. ID. NO. 7)
GAQVSTQKSGSHENQNFLTNGSNQTFTVINYYKDAASSSSAGQSLSMDPS  (SEQ. ID. NO. 8)
GAQVSTQKSGSHENQNILTNGSNQTFTVINYYKDAASSSSAGQSLSMDPS  (SEQ. ID. NO. 9)
GAQVSTQKSGSHENQNILTNGSNQTFTVINYYKDAASSSSAGQSLSMDPS  (SEQ. ID. NO. 10)
GAQISTQKSGSHEYQNILTNGSNQTFTVINYYKDAASSSSAGQSLSMDPS  (SEQ. ID. NO. 11)
GAQVSTQKSGSHENQNILTNGSNQTFTVINYYKDAASSSSAGQSFSMDPS  (SEQ. ID. NO. 12)
GAQVSTQKSGSHENQNILTNGSNQTFTVINYYKDAASSSSAGQSFSMDPS  (SEQ. ID. NO. 13)
GAQVSTQKSGSHENQNILTNGSNQTFTVINYYKDAASSSSAGQSFSMDPS  (SEQ. ID. NO. 14)
GAQVSTQKSGSHENQNILTNGSNQTFTVINYYKDAASSSSAGQSFSMDPS  (SEQ. ID. NO. 15)
GAQVSTQKSGSHENQNILTNGSHQTFTVINYYKDAASSSSASQSFSMDPS  (SEQ. ID. NO. 16)
GAQVSTQKSGSHENQNILTNGSNQTFTVINYYKDAASSSSASQSFSMDPS  (SEQ. ID. NO. 17)
GAQVSTQRSGSHENQNILTNGSHQTFTVINYYKDAASASSAGQSFSMDPS  (SEQ. ID. NO. 18)
GAQVSTQKSGSHENQNFLSNGSNQTFTVINYYKDAASSSSAGQSLSMDPS  (SEQ. ID. NO. 19)
GAQVSTQKSGSHEIQNMLTNGSHQTFTVINYYKDAASSSSAGQSLSMDPS  (SEQ. ID. NO. 20)
GAQVSTQKSGSHENQNILTNGSTQHFTVINYYKDAASSSSAGQSFSMDPS  (SEQ. ID. NO. 21)
GAQVSTQKSGSHENQNILTNGSTQHFTVINYYKDAASSSSAGQSFSMDPS  (SEQ. ID. NO. 22)
GAQVSTQKSGSHENQNILTNGSTQHFTVINYYKDAASSSSAGQSFSMDPS  (SEQ. ID. NO. 23)
GAQVSTQKSGSHENQTILTNGSTQPFTVINYYKDAASSSSAGQSFSMDPS  (SEQ. ID. NO. 24)
GAQVSTQKSGSHENQNILTNGSTQNFTVINYYKDAASSSSASQSFSMDPS  (SEQ. ID. NO. 25)
GAQVSTQKSGSHENQNILTNGSTHTFTVINYYKDAASSSSASQSFSMDPS  (SEQ. ID. NO. 26)
GAQVTRQQTGTHENANIATNGSHITYNQINFYKDSYAASASKQDFSQDPS  (SEQ. ID. NO. 27)
```

FIG 2

```
GAQVSRQNVGTHSTQNSVSNGSSLNYFNINYFKDAASSGASKLEFSQDPS  (SEQ. ID. NO. 28)
GAQVSRQNVGTHSTQNSVSNGSSLNYFNINYFKDAASSGASKLEFSQDPS  (SEQ. ID. NO. 29)
GAQVSRQNVGTHSTQNSVSNGSSLNYFNINYFKDAASSGASKLEFSQDPS  (SEQ. ID. NO. 30)
GAQVSRQNVGTHSTQNSVSNGSSLNYFNINYFKDAASSGASKLEFSQDPS  (SEQ. ID. NO. 31)
GAQVSRQNVGTHSTQNSVSNGSSLNYFNINYFKDAASSGASKLEFSQDPS  (SEQ. ID. NO. 32)
GAQVSRQNVGTHSTQNSVSNGSSLNYFNINYFKDAASSGASKLEFSQDPS  (SEQ. ID. NO. 33)
GAQVSRQNVGTHSTQNSVSNGSSLNYFNINYFKDAASSGASKLEFSQDPS  (SEQ. ID. NO. 34)
GAQVSRQNVGTHSTQNSVSNGSSLNYFNINYFKDAASSGASKLEFSQDPS  (SEQ. ID. NO. 35)
GAQVSRQNVGTHSTQNSVSNGSSLNYFNINYFKDAASSGASKLEFSQDPS  (SEQ. ID. NO. 36)
GAQVSRQNVGTHSTQNSVSNGSSLNYFNINYFKDAASSGASKLEFSQDPS  (SEQ. ID. NO. 37)
GAQVSRQNVGTHSTQNSVSNGSSLNYFNINYFKDAASSGASKLEFSQDPS  (SEQ. ID. NO. 38)
GAQVSRQNVGTHSTQNSVSNGSSLNYFNINYFKDAASSGASKLEFSQDPS  (SEQ. ID. NO. 39)
GAQVSRQNVGTHSTQNSVSNGSSLNYFNINYFKDAASSGASKLEFSQDPS  (SEQ. ID. NO. 40)
GAQVSRQNVGTHSTQNSVSNGSSLNYFNINYFKDAASSGASKLEFSQDPS  (SEQ. ID. NO. 41)
GAQVSRQNVGTHSTQNSVSNGSSLNYFNINYFKDAASSGASKLEFSQDPS  (SEQ. ID. NO. 42)
GAQVSRQNVGTHSTQNSVSNGSSLNYFNINYFKDAASSGASKLEFSQDPS  (SEQ. ID. NO. 43)
GAQVSRQNVGTHSTQNSVSNGSSLNYFNINYFKDAASSGASKLEFSQDPS  (SEQ. ID. NO. 44)
GAQVSRQNVGTHSTQNSVSNGSSLNYFNINYFKDAASSGASKLEFSQDPS  (SEQ. ID. NO. 45)
GAQVSRQNVGTHSTQNSVSNGSSLNYFNINYFKDAASSGASKLEFSQDPS  (SEQ. ID. NO. 46)
GAQVSRQNVGTHSTQNSVSNGSSLNYFNINYFKDAASSGASKLEFSQDPS  (SEQ. ID. NO. 47)
GAQVSRQNVGTHSTQNSVSNGSSLNYFNINYFKDAASSGASKLEFSQDPS  (SEQ. ID. NO. 48)
GAQVSRQNVGTHSTQNSVSNGSSLNYFNINYFKDAASSGASKLEFSQDPS  (SEQ. ID. NO. 49)
GAQVSRQNVGTHSTQNSVSNGSSLNYFNINYFKDAASSGASKLEFSQDPS  (SEQ. ID. NO. 50)
GTQVSRQNVGTHSTQNSVSNGSSLNYFNINYFKDAASSGASKLEFSQDPS  (SEQ. ID. NO. 51)
GAQVSRQNVGTHSTQNSGSNGSSLNYFNINYFKDAASSGASKLEFSQDPS  (SEQ. ID. NO. 52)
GAQVSRQNVGTHSTQNSVTNGSSLNYFNINYFKDAASSGASKLEFSQDPS  (SEQ. ID. NO. 53)
GAQVSRQNVGTHSTQNSVTNGSSLNYFNINYFKDAASSGASKLEFSQDPS  (SEQ. ID. NO. 54)
GAQVSRQNVGTHSTQNSVTNGSSLNYFNINYFKDAASSGASKLEFSQDPS  (SEQ. ID. NO. 55)
GAQVSRQNVGTHSTQNSVSGGSSLNYFNINYFKDAASSGASKLEFSQDPS  (SEQ. ID. NO. 56)
GAQVSRQNVGTHSTQNSVSHGSSLNYFNIHYFKDAASSGAFKLEFSQDPS  (SEQ. ID. NO. 57)
GAQVSRQNVGTHSTQNVVSSGSSLNYFNINYFKDAASSGASKLEFSQDPS  (SEQ. ID. NO. 58)
GAQVSRQNVGTHSTQNSVSNGSSLNFFNINYFKDAASSGASKLEFSQDPS  (SEQ. ID. NO. 59)
GAQVSRQNVGTHSTQNTVSNGSSLNFFNINYFKDAASSGASKLEFSQDPS  (SEQ. ID. NO. 60)
GAQVSRQNVGTHSTQNTVSNGSSLNYFNINYFKDAASSGASKLEFSQDPS  (SEQ. ID. NO. 61)
GAQVSRQNVGTHSTQNTVSNGSSLNYFNINYFKDAASSGASKLEFSQDPS  (SEQ. ID. NO. 62)
GAQVSRQNVGTHSTQNTVSNGSSLNYFNINYFKDAASSGASKLEFSQDPS  (SEQ. ID. NO. 63)
GAQVSRQNVGTHSTQNAVSNGSSLNYFNINYFKDAASSGASKLEFSQDPS  (SEQ. ID. NO. 64)
GAQVSRQNVGTHSTQNAVSNGSSLNYFNINYFKDAASSGASKLEFSQDPS  (SEQ. ID. NO. 65)
GAQVSRQNVGTHSTQNAVSNGSSLNYFNINYFKDAASSGASKLEFSQDPS  (SEQ. ID. NO. 66)
GAQVSRQNVGTHSTQNAVSNGSSLNYFNINYFKDAASSGASKLEFSQDPS  (SEQ. ID. NO. 67)
GAQVSRQNVGTHSTQNAVSNGSSLNYFNINYFKDAASSGASKLEFSQDPS  (SEQ. ID. NO. 68)
GAQVSRQNVGTHSTQNMVSNGSSLNYFNINYFKDAASSGASKLEFSQDPS  (SEQ. ID. NO. 69)
```

FIG 2
(CONTINUED)

```
GAQVSRQNVGTHSTQNMVSNGSSLNYFNINYFKDAASSGASKLEFSQDPS  (SEQ. ID. NO. 70)
GAQVSRQNVGTHSTQNMVSNGSSLNYFNINYFKDAASSGASKLEFSQDPS  (SEQ. ID. NO. 71)
GAQVSRQNVGTHSTQNSVSNGSSLNYFNINYFKDAASNGASKLDFTQDPS  (SEQ. ID. NO. 72)
GAQVSRQNVGTHSTQNSVSNGSSLNYFNINYFKDAASNGASKLEFTQDPS  (SEQ. ID. NO. 73)
GAQVSRQNVGTHSTQNSVSNGSSLNYFNINYFKDAASNGASKLEFSQDPS  (SEQ. ID. NO. 74)
GAQVSRQNVGTHSTQNAVTNGSSLNYFNINYFKDAASSGASRLDFSQDPS  (SEQ. ID. NO. 75)
GAQVSRQNVGTHSTQNAVTNGSRLNYFNINYFKDAASSGASRLDFSQDPS  (SEQ. ID. NO. 76)
GAQVSRQNVGTHSTQNAVSGGSSLNYFNINYFKDAASSGASRLDFSQDPS  (SEQ. ID. NO. 77)
GAQVSRQNVGTHSTQNAVSGGSSLNYFNINYFKDAASSGASRLDFSQDPS  (SEQ. ID. NO. 78)
GAQVSRQNVGTHSTQNTVTGGSSLNYFNINYFKDAASSGASRLDFSQDPS  (SEQ. ID. NO. 79)
GAQVSRQNVGTHTTQNAVSNGSSLNYFNINYFKDAASSGASRLDFSQDPS  (SEQ. ID. NO. 80)
GAQVSRQNVGTHSTQNTVANGSSLNYFNINYFKDAASNGASRLDFSQDPS  (SEQ. ID. NO. 81)
GAQVSRQNVGTHSTQNTVANGSSLNYFNINYFKDAASNGASRLDFSQDPS  (SEQ. ID. NO. 82)
GAQVSRQNVGTHSTQNTVANGSSLNYFNINYFKDAASNGASRLDFSQDPS  (SEQ. ID. NO. 83)
GAQVSRQNVGTHSTQNTVANGSSLNYFNINYFKDAASSGASRLDFSQDPS  (SEQ. ID. NO. 84)
GAQVSRQNV-THSTQNAVSNGSSLNYFNINYFKDAASSGASRLDFSQDPS  (SEQ. ID. NO. 85)
GAQVSRQNVGTHSTQNAVSNGSSLNYFNINYFKDAASSGASRLDFSQDPS  (SEQ. ID. NO. 86)
GAQVSRQNVGTHSTQNAVTNGSSLNYFNINYFKDAASSGASRLDFSQDPS  (SEQ. ID. NO. 87)
GAQVSRQNVGTHSTQNAVTNGSSLNYFNINYFKDAASSGASRLDFSQDPS  (SEQ. ID. NO. 88)
GAQVSRQNVGTHSTQNSVSNGSSLNYFNINYFKDAASSGASRLDFSQDPS  (SEQ. ID. NO. 89)
GAQVSRQNVGTHSTQNSVSNGSSLNYFNINYFKDAASSGASRLDFSQDPS  (SEQ. ID. NO. 90)
GAQVSRQNVGTHSTQNMVSNGSSLNYFNINYFKDAASSGASRLDFSQDPS  (SEQ. ID. NO. 91)
GAQVSRQNVGTHSTQNSVSNGSSLNYFNINYFKDAASSGASRLDFSQDPS  (SEQ. ID. NO. 92)
GAQVSRQNVGTHSTQNSVSNGSSLNYFNINYFKDAASSGASRLDFSQDPS  (SEQ. ID. NO. 93)
GAQVSRQNVGTHSTQNSVSNGSSLNYFNINYFKDAASSGASRLDFSQDPS  (SEQ. ID. NO. 94)
GAQVSRQNVGTHSTQNSVSNGSSLNYFNINYFKDAASSGASRLDFSQDPS  (SEQ. ID. NO. 95)
GAQVSRQNVGTHSTQNSVSNGSSLNYFNINYFKDAASHGASKLDFSQDPS  (SEQ. ID. NO. 96)
GAQVSRQNVGTHSTQNSVSNGSSLNYFNINYFKDAASHGASKLDFSQDPS  (SEQ. ID. NO. 97)
GAQVSRQNVGTHSTQNTVSNGSSLNYFNINYFKDAASHGASKLDFSQDPS  (SEQ. ID. NO. 98)
GAQVSNQNVGTHSTQNPVSNGSSLNYFKINYFKDAASNGASKLEFSQDPS  (SEQ. ID. NO. 99)
```

| Rhino 14 | GAQVStQksGsHenQ | (SEQ.ID.NO.102) |
| Rhino 1a | GAQVSrQnvGtHstQ | (SEQ.ID.NO.103) |
| Rhino 2  | GAQVSrQnvGtHstQ | (SEQ.ID.NO.104) |
| Rhino 9  | GAQVSrQnvGtHstQ | (SEQ.ID.NO.105) |
| Rhino 15 | GAQVSrQnvGtHstQ | (SEQ.ID.NO.106) |
| Rhino 16 | GAQVSrQnvGtHstQ | (SEQ.ID.NO.107) |
| Rhino 85 | GAQVSrQnvGtHstQ | (SEQ.ID.NO.108) |
| Rhino 89 | GAQVSrQnvGtHstQ | (SEQ.ID.NO.109) |
| Rhino 29 | GAQVSrQnvGtHstQ | (SEQ.ID.NO.110) |

FIG 5

```
Peptide 1:GAQVSTQKSGSHENQNILTNGSNQTFTVINY (SEQ.ID.NO. 1)
          1113111221211222422111165222111
%Identity:  1=100, 2=96, 3=92, 4=88, 5=80, 6=48
```
(Group 1: 25 sequences)

```
Peptide 2:GAQVSRQNVGTHSTQNMVSNGSSL (SEQ.ID.NO. 2)
          111111111211211152431111
%Identity:  1=100, 2=99, 3=92, 4=83, 5=58
```
(Group 2: 72 sequences)

FIG 6

HRV14 neutralization by antibodies to HRV14 VP4 N-terminus

FIG 7

HRV16 neutralization by
antibodies to HRV14 VP4

FIG 8

HRV29 neutralization by antibodies to HRV14 VP4

- 8hr, RT
- 8hr, RT, preimmune

FIG 9

HRV neutralization by antibodies to peptide
representing the group 2 HRV VP4

■ HRV14, 8hr, RT
☐ HRV14, 2hr, RT
▨ HRV14, 8hr, RT, preimmune
■ HRV16, 2hr, RT
☰ HRV16, 2hr, 35¡C
▥ HRV16, 2hr, 35¡C, preimmune

RHINOVIRUS VACCINES

CROSS-REFERENCE TO RELATED APPLICATIONS

This application claims the benefit of U.S. Provisional Application No. 60/645,353, filed Jan. 19, 2005, which is incorporated herein by reference.

This invention was supported in part by grant number R01-GM010704-43 from the National Institutes of Health (NIH). The U.S. Government may have certain rights in the invention.

FIELD OF THE INVENTION

The present invention relates generally to vaccines against viruses. More specifically, the present invention relates to vaccines against picornaviruses, including rhinoviruses, and other related and non-related pathogenic animal viruses. In addition, the present invention relates to methods of designing and producing vaccines against viruses and, in certain embodiments, against rhinoviruses and other related and non-related pathogenic animal viruses.

BACKGROUND OF THE INVENTION

Picornaviruses are among the largest of animal virus families that cause major diseases, such as poliomyelitis (poliovirus), hepatitis (hepatitis A virus), foot-and-mouth disease (FMDV), severe respiratory disease (coxsackievirus), inflammation of cardiac tissue (cardioviruses), and the common cold (human rhinovirus). Rhinoviruses, in particular, are the major causative agents of the common cold in humans. It has been estimated that the cost of this illness to the United States economy is $40 billion per year. Therefore, the prevention or cure of the common cold remains a goal of high impact.

For numerous reasons, at this time, there is no commercially-available vaccine for human rhinovirus infection. Among such reasons, it is well documented that rhinoviruses exhibit more than 100 serotypes. Each serotype is generally defined by the recognizable antigenic determinants (i.e., epitopes) which exist on the surface of the viruses. Accordingly, rhinoviruses may exhibit any of more than 100 immunologically distinct serotypes, which renders producing an effective vaccine against such viruses problematic. Indeed, using currently-available technology, patients must be injected with attenuated or inactive viruses representing each serotype or several peptides for each serotype to elicit sufficient protection against the common cold—making vaccination against rhinovirus unfeasible.

To further complicate matters, the available epitopes on such rhinoviruses are not linear; rather, the epitopes are three-dimensional. More particularly, it is believed that the major antigenic sites on the virus consist of several peptide loops. As a result, antibodies raised against such epitopes recognize a three-dimensional structure rather than a linear polypeptide or portion thereof.

Indeed, in the case of human rhinovirus 14, for example, antibodies raised against correspondingly linear peptides are usually non-reactive against the authentic virion. Therefore, for many viruses, such as rhinoviruses, attenuated or intact (dead) virions must be used for vaccination. Given that there are at least 100 serotypes of human rhinoviruses, such an approach is impractical (if not impossible).

The present invention circumvents many of the above problems and offers novel methods and compositions to generate and design effective peptide vaccines against highly variable viruses, including human rhinoviruses (and other picornaviruses).

SUMMARY OF THE INVENTION

The present invention relates generally to vaccines against viruses and, more specifically, against picornaviruses. In certain preferred embodiments, the invention relates generally to vaccines against rhinoviruses. In addition, the invention provides methods of designing and producing vaccines, including vaccines against picornaviruses and, in certain preferred embodiments, against rhinoviruses (and related and un-related pathogenic animal viruses).

Using mass spectrometry analysis and limited proteolysis, it has been determined that certain buried portions of the rhinovirus capsid (and other picornaviruses) are transiently exposed on the surface during a "breathing" process. The inventor has found that such buried portions are, generally, genetically conserved among numerous rhinovirus serotypes. More importantly, the inventor has discovered that antibodies may be generated against such transiently exposed capsid portions and/or variations thereof, which are capable of neutralizing and cross-reacting with multiple and different serotypes of rhinoviruses.

Accordingly, the invention provides, among other things, methods of identifying and designing novel peptide vaccines using high resolution peptide analysis such as, but not limited to, matrix-assisted laser desorption/ionization ("MALDI") mass spectroscopy ("MS") and limited proteolysis. More specifically, the invention provides methods of using such techniques to identify buried and conserved portions of virus capsids, which may be exploited to generate pan-serotypic peptide vaccines. In certain embodiments, for example, the invention encompasses methods of using the N-termini of certain viral capsid proteins, and/or functional equivalents thereof, in a peptide display system to raise neutralizing antibodies thereto. Still further, such embodiments include the use of the N-termini of VP4 proteins, such as in a peptide vaccine and/or functional equivalents thereof, to produce a desirable immune response in a subject. Of course, the invention further includes the vaccines described herein, and those which may be designed and/or produced using the methods (and variations thereof) contemplated by the present invention.

The above-mentioned and additional features of the present invention are further illustrated in the Detailed Description contained herein. All references disclosed herein, including U.S. patents, are hereby incorporated by reference in their entirety as if each was incorporated individually.

BRIEF DESCRIPTION OF THE FIGURES

FIG. 1: Sequence alignment of amino acid sequences residing on transiently exposed portions of the N-termini of VP4 proteins within human rhinovirus (HRV) Group 1 (as defined herein).

FIG. 2: Sequence alignment of amino acid sequences residing on transiently exposed portions of the N-termini of VP4 proteins within human rhinovirus (HRV) Group 2 (as defined herein).

FIG. 3: A chart showing the conservation of amino acid residues at each position along the VP0 (VP4 and VP2) and VP1 polypeptides. The externally exposed regions of the capsid are denoted by bars at the top.

FIG. 4: Sequence alignment of portions of the N-termini of VP4 proteins (from a limited number of the more than 100 different serotypes of human rhinovirus).

FIG. 5: Non-limiting examples of rhinovirus peptide vaccines of the present invention. The degree of identity is shown for each residue relative to the numerous VP4 amino acid sequences which were considered in designing such peptide vaccines.

FIG. 6: A graph showing that antibodies raised against Peptide 1 (defined below) are capable of neutralizing human rhinovirus 14 infection.

FIG. 7: A graph showing that antibodies raised against Peptide 1 are capable of neutralizing a different serotype, human rhinovirus 16.

FIG. 8: A graph showing that antibodies raised against Peptide 1 are capable of neutralizing yet another serotype, human rhinovirus 29.

Figure 3:
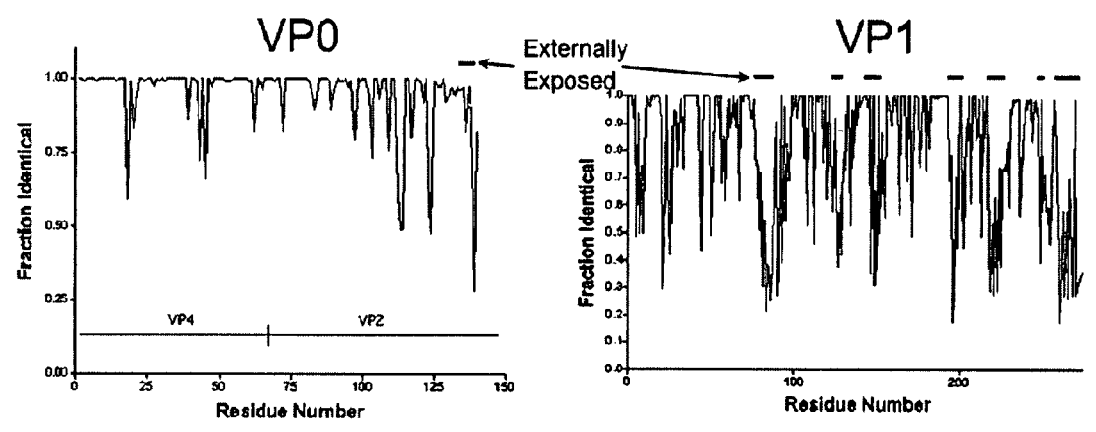

FIG. 9: A graph showing that antibodies raised against Peptide 2 are capable of negatively affecting the viability of human rhinovirus 14. Peptide 2 was designed based on the sequence alignment of HRV Group 2 (shown visually in FIGS. 2 and 3).

BRIEF DESCRIPTION OF THE SEQUENCE LISTING

SEQ ID NO. 1: Peptide 1, which represents a non-limiting example of a peptide vaccine of the present invention.

SEQ ID NO. 2: Peptide 2, which represents a second non-limiting example of a peptide vaccine of the present invention.

SEQ ID NO. 3-27: The amino acid sequences of the N-termini regions of VP4 capsid proteins within HRV Group 1 (described below).

SEQ ID NO. 28-99: The amino acid sequences of the N-termini regions of VP4 capsid proteins within HRV Group 2 (described below).

SEQ ID NO. 100: A non-limiting example of a nucleic acid sequence encoding Peptide 1 (SEQ ID NO: 1).

SEQ ID NO. 101: A non-limiting example of a nucleic acid sequence encoding Peptide 2 (SEQ ID NO: 2).

DETAILED DESCRIPTION OF THE INVENTION

The following will describe in detail several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

The present invention relates generally to vaccines against viruses and, in certain preferred embodiments, rhinoviruses (as well as other picornaviruses). In addition, the invention provides methods of designing and producing such vaccines.

DEFINITIONS

The following words and phrases shall have the meanings set forth below.

The term "adjuvant" refers to a composition which may enhance the immune response of the subject to whom a vaccine of the present invention is administered, i.e., by acting as a non-specific immunostimulator. An adjuvant may also be used to elicit an immune response more rapidly.

The term "administering" means bringing the immune response cells of a subject in contact with an immunogenic peptide vaccine of the present invention. In most cases, such "administering" takes place either by subcutaneous or intramuscular injection of the immunogenic peptide vaccine composition into the subject. More recently, it has been shown that vaccination can also be performed using intranasal administration. Those of ordinary skill in the art will appreciate that the above modes of administering a vaccine are provided for purposes of illustration and other modes may be employed in practicing the present invention.

The term "carrier molecule" refers to an immunogenic composition to which a peptide vaccine of the present invention may be linked, conjugated, or otherwise associated to enhance and/or expedite an immune response.

The term "epitope" or "antigenic determinant," relative to a peptide, refers to a portion of an amino acid sequence which will generate a B- and/or T-cell mediated immune response against such peptide.

The terms "functional equivalent" and "functionally equivalent" mean an amino acid sequence for a particular immunogenic peptide having substantially equivalent (or greater) biological activity to another amino acid sequence. Such functionally equivalent amino acid sequences may be naturally occurring (native) or non-native. The relevant biological activity is immunological activity, i.e., the ability to elicit an immune response in a subject to whom the functionally equivalent or original immunogenic peptide is administered.

The term "immune response" refers to a humoral immune response (such as production of antibodies against an immunogenic epitope) or a cellular immune response (such as a cytotoxic T cell response).

The terms "immunization," "immunizing," and "immunized" mean the use of a peptide vaccine or vaccines contemplated by the present invention to induce an immune response by the immune response cells of a subject.

The term "immunocompetent subject" refers to a mammal having an immune system that, upon exposure to an immunogenic epitope, is capable of mounting a cellular and/or humoral immune response against the immunogenic epitope.

The term "non-native," relative to an immunogenic peptide or epitope, means the amino acid sequence of the epitope differs by one or more amino acids from the amino acid sequence of the same immunogenic epitope as it is found in nature. The "non-native" amino acid sequence may comprise an immunogenic epitope having a variant amino acid sequence which contains one or more "conservative" or "non-conservative" amino acid substitutions, amino acid insertions or deletions, or in some cases may have additional amino acids at the N- or C-terminal end of the peptide.

The term "peptide vaccine" refers to an immunogenic peptide of the present invention, which may optionally be conjugated or otherwise associated with a suitable carrier molecule and/or contained within an adjuvant.

The term "substantially isolated and purified", as it relates to a peptide vaccine of the present invention, means that such peptide vaccine (before it is conjugated or otherwise associated with a suitable carrier molecule, added to an adjuvant, or otherwise manipulated to produce a finished vaccine composition) is substantially separated from its native environment—if such environment exists. For example, in certain embodiments, a substantially isolated and purified form of a peptide vaccine may constitute at least 40% (wt) of the total composition in which it resides (before such peptide vaccine is added to buffers, adjuvants, carrier molecules, or other delivery-related compositions), or preferably at least 60% (wt), or more preferably at least 80% (wt), or still more preferably at least 90% (wt). If such peptide vaccines are produced and/or expressed in connection with carrier proteins, fusion proteins, or other compositions, such additional compositions should be disregarded for the purpose of determining whether such peptide vaccines are in a substantially isolated and purified form.

Rhinoviruses

Human rhinovirus infections begin with binding of the virion to its receptor on the outside of a cell, translocation of the virus particles into the cell, and the release of its genomic material into the cytoplasm. The virus particle must, therefore, be flexible enough to allow such cellular binding and disassembly of the virions, yet stable enough to survive in the extracellular milieu.

The human rhinovirus is non-enveloped and has an approximately 300 Å diameter protein shell that encapsidates a single-stranded, plus-sense, RNA genome of about 7,200 bases. The human rhinovirus 14 ("HRV14") capsid exhibits a pseudo T=3 (P=3) icosahedral symmetry and consists of 60 copies each of four viral proteins: VP1, VP2, VP3, and VP4. Proteins VP1, VP2, and VP3 have eight-stranded, anti-parallel β-barrel motifs and comprise most of the capsid structure. VP4 is of lower molecular size than proteins VP1, VP2 and VP3, has an extended structure, and lies at the RNA/capsid interface making it the most interior capsid protein.

Limited Proteolysis and MALDI-MS Analysis

Modern mass spectrometry techniques, such as MALDI-MS and electrospray ionization (ESI-MS), combined with limited proteolysis, have been used to monitor the dynamic nature of virus particles. More specifically, for example, viral capsid mass mapping experiments have been used to obtain information regarding the dynamic nature of the viral capsid in the presence of anti-viral compounds, such as WIN 52084 (Lewis, Bothner et al. 1998). In these experiments, peptide fragments from limited proteolysis were identified using MALDI-MS, thereby elucidating the relative accessibility of capsid regions containing specific cleavage sites. Such experiments have shown that the human rhinovirus 14 capsid, for example, transiently extrudes internal VP1 and VP4 N-termini in a "breathing" process (Lewis, Bothner et al. 1998).

The present invention exploits the "breathing" process observed in many viruses, including rhinoviruses. More particularly, the invention provides that certain internal, buried, and/or non-exposed portions of viral capsids (which are only transiently exposed) may be identified using readily available tools, such as, but not limited to, limited proteolysis and MALDI-MS. In certain embodiments, the invention provides that such techniques may be employed to identify (and/or sequence) such transiently exposed portions of viral capsids of a target virus species. Preferably, such analysis is conducted across a majority of the serotypes which comprise such virus species.

In general, mass spectrometry provides a means of "weighing" individual molecules by ionizing the molecules in vacuo and making them "fly" by volatilization. For mass spectrometry analysis of a target capsid polypeptide, the polypeptide is first subjected to site-specific proteolytic degradation with a protease having known cleavage sites, such as trypsin, chymotrypsin, or others known in the art. Following such digestion, the protein fragments may be solubilized in an appropriate solution or reagent system. The type of solution or reagent system, e.g., comprising an organic or inorganic solvent, will depend on the properties of the polypeptide and the type of mass spectrometry performed (which are well known to those of ordinary skill in the art).

Using readily available MALDI-MS equipment, for example, mass spectrometry may then be conducted. The methods by which such analyses are carried out are well known to those of ordinary skill in the art. See, e.g., Vorm et al. (1994) Anal. Chem. 66:3281 (for MALDI-MS); and Valaskovic et al. (1995) Anal. Chem. 67:3802 (for ESI). Mass spectrometry of peptides is further disclosed in, for example, U.S. Pat. No. 6,271,037 by Chait et al., which is hereby incorporated by reference in its entirety.

Previous studies showing that virus structures are indeed dynamic and that certain portions thereof are transiently exposed provide further non-limiting examples of how such limited proteolysis and MALDI-MS experiments may be conducted. See, e.g., Lewis, J. K., et al. (1998) *Proc. Natl. Acad. Sci.* USA 95, 6774-78 (referenced above); and Bothner, B., et al. (1998) *J. Biol. Chem.* 273, 673-76 (describing proteolytic time-course experiments involving the Flock house virus (FHV) to show, in connection with certain x-ray data, that portions of its capsid proteins are transiently exposed on the viral surface).

While certain preferred embodiments of the present invention provide methods of designing peptide vaccines against rhinoviruses, the invention may further be utilized to design peptide vaccines against other picornaviruses, which have recently been shown to exhibit similar types of capsid dynamics as are described herein relative to human rhinoviruses (i.e., "capsid breathing"). For example, in the case of swine vesicular disease virus (SVDV) and coxsackievirus A9 (C A9), polyclonal antibodies have been raised against the whole virus in pigs and rabbits, which were reported to demonstrate a strong reaction to peptides representing the N-termini of VP1 capsid proteins of SVDV and C A9, respectively. These results imply that "capsid breathing" may be a phenomenon common to many proteinaceous capsids (See Pulli, T., et al. (1998) "Antigenic sites of coxsackievirus A9" *Virology* 240: 202-212; and Jimenez-Clavero, M. A., et al. (2000) "Immune Recognition of Swine vesicular disease virus structural proteins: Novel antigenic regions that are not exposed in the capsid" *Virology* 270: 76-83).

Upon identifying such transiently exposed regions of capsid proteins of the subject virus, amino acid sequence information may be obtained for such regions. In some cases, the amino acid sequence information may be published and/or otherwise available within a public database, such as those maintained by the National Center for Biotechnology Information (i.e., GenBank, Entrez, etc.).

If the amino acid sequences of such transiently exposed regions of capsid proteins are not publicly-accessible, certain amino acid sequencing procedures and equipment may be employed to obtain such information. For example, a Perkin Elmer Applied Biosystems (Foster City, Calif.) Model 494 Procise® protein/peptide sequencer, along with a Perkin Elmer Applied Biosystems Model 140C PTH Amino Acid Analyzer, may be utilized to sequence such transiently exposed regions of capsid proteins. The chemical process employed by such protein sequencer to determine the amino acid sequence of a protein is derived from the Edman degradation method. In this method, phenylisothiocyanate (PITC) reacts with the amino acid residue located at the N-terminus of the subject protein (under certain basic conditions imparted by the presence of n-methylpiperidine/methanol/water) to form a phenylthiocarbamyl derivative (PTC-protein). Trifluoroacetic acid (TFA) then cleaves the first amino acid, creating an anilinothialinone derivative (ATZ-amino acid) and leaving a new N-terminus for the next Edman degradation cycle.

Next, the ATZ-amino acid is removed by extraction with N-butyl chloride and converted into a phenylthiohydantoin derivative (PTH-amino acid) using 25% TFA/water. The PTH-amino acid is transferred to a reverse-phase C-18 column for spectrophotometric analysis (at 270 nm). A standard mixture of 19 PTH-amino acids is also injected onto the column for separation (usually as the first cycle of the sequencing procedure). A chromatogram for the standard mixture of 19 PTH-amino acids is generated, which provides standard retention times of such amino acids. Additionally, high-performance liquid chromatograms (HPLCs) are collected for each cycle of Edman degradation of the test protein—using a computer data analysis system. The chromatogram for the residue of interest (of the test protein) is compared with the chromatogram generated from the standard mixture by overlaying one on top of the other. At such time, the amino acid for the residue of interest may be determined. This process is repeated sequentially to provide the N-terminal sequence of the subject capsid protein.

Identifying Vaccine Targets

Upon identifying and sequencing such transiently exposed, internal portions of the target viral capsid proteins (across the serotypes of interest), the invention provides that comparative analyses may be conducted to identify areas of preferred homology, i.e., areas exhibiting preferred sequence conservation. In general, areas exhibiting at least a minimum level of sequence conservation are, preferably, used to generate the peptide vaccines described herein. Specifically, the invention contemplates that peptide vaccines may be designed which are, preferably, functionally equivalent to at least a majority of such areas exhibiting preferred levels of sequence conservation. That is, such peptide vaccines preferably constitute the "common denominator" among such areas of sequence conservation within the transiently exposed regions of capsid proteins across the serotypes of interest.

The invention provides that designing one or more peptide vaccines based on such areas exhibiting a certain level of sequence conservation increases the potential effectiveness of such peptide vaccines. For example, when the variability among portions of capsid peptides (across the serotypes of interest) is minimized, peptide vaccines based on such portions may comprise a correspondingly maximum number of conserved residues. Such maximum number of conserved residues within the peptide vaccine increases the probability that administering such vaccine to a subject will elicit a desirable immune response. More particularly, such maximum number of conserved residues within the peptide vaccine increases the chance that the vaccine will elicit a desirable immune response against a majority of the serotypes of interest.

The means by which capsid regions exhibiting preferred sequence conservation may be identified are well known in the art. Preferably, for example, the amino acid sequence data corresponding to the same transiently exposed regions (as determined using, for example, the methods described herein) of a particular capsid protein are analyzed electronically (across each serotype of interest). For example, the sequence data for each analyzed serotype may be electronically compared, or "aligned," to identify areas of preferred sequence conservation. Such methods are well known in the art and, for example, are often conducted using readily available software programs, such as BLAST.

In addition to mere residue-to-residue matches among a plurality of amino acid sequences (which correspond to the transiently exposed capsid regions among the serotypes of interest as discussed herein), several other factors may be considered in identifying such preferred areas of sequence conservation. For example, the invention provides that (i) the length of the sequences, (ii) residue composition (including the hydrophobicity, charge, R-group, antigenicity, and other characteristics of each residue and of the sequence as a whole), (iii) percent conservation for each residue comprising a given set of sequences, (iv) position of certain residues which exhibit relatively less (or more) conservation among the analyzed serotypes, and/or (v) other relevant factors known in the art may be considered.

For example, the invention contemplates that the nature of variability among certain residues within a given set of sequences of transiently exposed capsid regions may be considered. More particularly, the invention contemplates that certain types of variability at one or more residue locations among a set of sequences may affect the immunogenicity of a peptide vaccine more than others. For example, it is known that certain amino acid substitutions are possible without substantially affecting the immunogenic character of the fragment.

For purposes of illustration, substitutions may be grouped into six classes based on common side chain (or "R-group") properties and the highest frequency of substitution in homologous proteins in nature, as determined, for example, by a standard Dayhoff frequency exchange matrix. The table below represents an example of such classes:

| Class | Residues | Description |
| --- | --- | --- |
| Class I | Cysteine | |
| Class II | Serine, Threonine, Proline, Hydroxyproline, Alanine, and Glycine | Small aliphatic and OH-group side chains |
| Class III | Asparagine, Aspartic acid, Glutamic acid, and Glutamine | Neutral and negatively charged side chains capable of forming hydrogen bonds |
| Class IV | Histidine, Arginine, and Lysine | Basic polar side chains |
| Class V | Isoleucine, Valine, Leucine, and Methionine | Branched aliphatic side chains (except Methionine) |
| Class VI | Phenylalanine, Tyrosine, and Tryptophan | Aromatic side chains |

In addition, each class may further include related amino acid analogs, such as, for example, ornithine, homoarginine, N-methyl lysine, dimethyl lysine, or trimethyl-lysine in class IV, and a halogenated tyrosine in Group VI. Further, for example, the classes may include both L and D stereoisomers (although, in certain embodiments, L-amino acids are preferred for substitutions).

In light of the foregoing, it is envisaged that variability within a class of residues, for example, at a particular location among serotypes of interest may not negatively influence the effectiveness of a peptide vaccine based thereon. For purposes of illustration only, if a transiently exposed capsid protein of a first serotype includes a serine residue at a particular location and a second serotype includes a threonine residue at the same location, the invention provides that a peptide vaccine including serine, threonine, or any other residue of Class II above at the corresponding location may elicit a substantially similar immune response against the first and second serotypes.

Importantly, the invention provides that such variability within classes of amino acid residues may, optionally, be considered in identifying areas of preferred sequence conservation among a plurality of serotypes. For example, the invention contemplates that variability within a class of residues at a particular location may be disregarded (i.e., considered a conserved residue), considered partly conserved, or some variation thereof. For purposes of illustration only, variability at a particular location which spans two or more classes of residues may be assigned a value of one (v=1), whereas variability at a particular location within a single class of residues may be assigned a value between zero and one (such as v=0.25, 0.50, or 0.75). In such example, of course, sequence alignments among a plurality of serotypes producing the lowest total variability number are preferred, i.e., may represent areas of sequence conservation which may serve as the basis for designing a peptide vaccine described herein.

The invention further provides that certain serotypes may be excluded from such analysis. That is, it is envisaged that, in some cases, a majority of serotypes may exhibit desired sequence conservation in a particular area of the identified transiently exposed capsid protein, whereas others may not (i.e., certain serotypes of a virus species may be statistical outliers). The invention provides that such areas of desired conservation among a majority of such serotypes may be considered, while the other serotypes that do not exhibit desired conservation levels in the corresponding area of the transiently exposed capsid protein may be ignored. In such instances, the designed peptide vaccine, preferably, is capable of eliciting an immune response against the majority of such serotypes, while minimizing the ineffectiveness of such immunization to only the minority of serotypes not exhibiting preferred sequence conservation in the target area.

In still further embodiments, the invention provides that peptide vaccines may be designed for two or more groups of serotypes. More particularly, the invention anticipates that some regions within transiently exposed portions of the capsid proteins may exhibit sequence conservation within two, three, four, or more groups. For purposes of illustration, it is envisaged that a particular region within transiently exposed portions of the capsid proteins may exhibit preferred conservation within a subset of serotypes, wherein two or more subsets of distinct sequences (and corresponding sequence conservation) within a virus species may exist. In such embodiments, the invention provides that peptide vaccines may be designed and used to address each (or limited number of) such subsets of conserved sequences. It is further predicted that such groups of serotypes may exhibit preferred sequence conservation in the same or different regions of one or more transiently exposed capsid proteins.

Designing the Peptide Vaccines

Upon identifying one or more areas of preferred sequence conservation among the serotypes of interest, the peptide vaccine may be designed. Preferably, the peptide vaccine constitutes a functional equivalent of a majority of the conserved regions which are identified within the transiently exposed portions of the capsid proteins. In designing such peptide vaccines, the interchangeability of certain residues within each class of amino acids is, preferably, considered (as discussed above). That is, the invention provides that the peptide vaccine composition should be designed in such a way that renders it as similar as possible to at least a majority of such conserved regions across the serotypes of interest.

The "similarity" of the peptide vaccine to the target capsid regions, preferably, is based on several factors, such as (i) the percent identity at each residue in relation to the same locations within each transiently exposed capsid protein across the serotypes of interest and (ii) the biological, or immunological, similarity of such peptides to such target capsid regions. In determining whether any given difference between a residue in the peptide vaccine and target capsid protein is similar or dissimilar, the various classes of amino acids discussed above may be considered. For example, differences between a peptide vaccine and a target capsid region which is confined to a single class of amino acids may not be considered significant, i.e., such portions of the peptide vaccine and target capsid protein may be considered similar. In contrast, for example, differences between a peptide vaccine and a target capsid region which spans two or more classes of amino acids may be considered significant, i.e., such portions of the peptide vaccine and target capsid protein may be considered dissimilar.

Still further, for example, the invention provides that the hydropathic index of amino acids may be considered in designing peptide vaccines of the present invention. In general, the hydropathic profile of a protein is calculated by assigning each amino acid a numerical value ("hydropathy index") and then repetitively averaging such values along the peptide chain. More particularly, the invention contemplates that certain amino acids may be substituted with other amino acids having a similar hydropathic index or score and still obtain a functionally equivalent protein. The means by which such hydropathic scores are assigned to each residue are not particularly germane to the present invention, and are well known to those of ordinary skill in the art. See, e.g., Hopp T. P. and Woods K. R. (1981) Prediction of protein antigenic determinants from amino acid sequences. *Proc. Nat. Acad. Sci. USA* 78(6): 3824-28; and Kyte J. and Doolittle R. F. (1982) A Simple Method for Displaying the Hydropathic Character of a Protein. *J. of Mol. Bio.* 157(6): 105-142.

For purposes of illustration, however, the table below lists the hydropathic index for certain amino acid residues:

| Amino Acid | Hydropathy Index |
| --- | --- |
| Alanine | 1.8 |
| Arginine | −4.5 |
| Asparagine | −3.5 |
| Aspartic acid | −3.5 |
| Cysteine | 2.5 |
| Glutamine | −3.5 |
| Glutamic Acid | −3.5 |
| Glycine | −0.4 |
| Histidine | −3.2 |
| Isoleucine | 4.5 |
| Leucine | 3.8 |
| Lysine | −3.9 |
| Methionine | 1.9 |
| Phenylalanine | 2.8 |
| Proline | −1.6 |
| Serine | −0.8 |
| Threonine | −0.7 |

| Amino Acid | Hydropathy Index |
|---|---|
| Tryptophan | −0.9 |
| Tyrosine | −1.3 |
| Valine | 4.2 |

Accordingly, the invention provides that peptide vaccines may be designed, wherein the average variability between each vaccine residue and each corresponding location in the target capsid protein across the serotypes of interest is within a preferred range. In certain embodiments, for example, peptide vaccines may be designed wherein each (or a majority) of the amino acids which comprise such peptide vaccine exhibit hydropathic indices within +/−2.0 of each corresponding residue in the target capsid proteins across the serotypes of interest, and those which are within +/−1.0 are particularly preferred, and those within +/−0.5 are even more particularly preferred. Still further, the average hydropathic index of the peptide vaccine as a whole may be considered in relation to the hydropathic index for each target capsid region (as a whole) across the serotypes of interest.

In addition to optimizing the functional equivalency of the peptide vaccine, several other factors may be considered in designing its composition. For example, the specific amino acid composition of the vaccine may reflect certain additional pharmacologic considerations, such as solubility, stability, allerginicity, and other properties known in the art. Furthermore, it is preferred that the epitopes which are contained within the peptide vaccine be unique. That is, it is preferred that an immune response generated to the specific epitopes of the peptide vaccines shows little or no cross-reactivity with other antigens, such as, of course, epitopes which may naturally exist within a subject.

The amino acid sequences of the peptide vaccines described herein may further include certain additional residues (which are not correlated to the target capsid regions), such as additional N- or C-terminal amino acids (or other branched segments within the peptide vaccine). For example, the peptide vaccine may comprise a linker sequence which enables conjugation to a carrier molecule. Preferably, the addition of such N- or C-terminal sequences (or branched sequences within the vaccine component) do not significantly mitigate the immunogenicity of the vaccine. Still further, in designing the peptide vaccines of the present invention, it will be appreciated by those of ordinary skill in the art that the peptide or peptides employed in the vaccine may comprise native sequences, non-native sequences, or combinations thereof.

Vaccine Production

Upon designing a peptide vaccine in accordance with the present invention, it may subsequently be produced using any suitable means known in the art (currently existing or discovered hereafter). For purposes of illustration, the peptide vaccines may be expressed, via recombinant DNA technology, in host cells such as bacteria, yeast, plant, insect, and cultured mammalian cells.

A variety of host-expression vector systems may be used to express a nucleotide sequence encoding a peptide vaccine of the present invention. In certain embodiments, for example, the peptide vaccine-encoding sequence may be designed to express such peptide as a soluble or secreted molecule, wherein the soluble peptide may be recovered from the culture media. Purification from such expression systems may be accomplished using appropriate detergents, lipid micelles, and methods well known to those skilled in the art.

As used herein, the term "peptide vaccine-encoding sequence", and similar terms and phrases, refers to any and all nucleic acid sequences the expression of which produces a peptide vaccine of the present invention (or any part or precursor thereof). After designing a particular peptide vaccine of the present invention and identifying the preferred amino acid sequence thereof, the various nucleic acid sequences that may be used to express such peptide vaccine in an appropriate host are well known to those of ordinary skill in the art. Of course, in view of the degeneracy of the genetic code, considerable sequence variation is possible among the nucleic acid sequences encoding a particular peptide vaccine of the present invention. For purposes of illustration only, any of the degenerate codons referenced in the table below (or others known in the art) may be used to express the various amino acid residues that comprise, for example, Peptide Vaccine 1 (SEQ ID NO: 1) and Peptide Vaccine 2 (SEQ ID NO: 2), which are described further below.

| | | | | | | | |
| --- | --- | --- | --- | --- | --- | --- | --- |
| TTT | Phe | TCT | Ser | TAT | Tyr | TGT | Cys |
| TTC | Phe | TCC | Ser | TAC | Tyr | TGC | Cys |
| TTA | Leu | TCA | Ser | TAA | STOP | TGA | STOP |
| TTG | Leu | TCG | Ser | TAG | STOP | TGG | Trp |
| CTT | Leu | CCT | Pro | CAT | His | CGT | Arg |
| CTC | Leu | CCC | Pro | CAC | His | CGC | Arg |
| CTA | Leu | CCA | Pro | CAA | Gln | CGA | Arg |
| CTG | Leu | CCG | Pro | CAG | Gln | CGG | Arg |
| ATT | Ile | ACT | Thr | AAT | Asn | AGT | Ser |
| ATC | Ile | ACC | Thr | AAC | Asn | AGC | Ser |
| ATA | Ile | ACA | Thr | AAA | Lys | AGA | Arg |
| ATG | Met* | ACG | Thr | AAG | Lys | AGG | Arg |
| GTT | Val | GCT | Ala | GAT | Asp | GGT | Gly |
| GTC | Val | GCC | Ala | GAC | Asp | GGC | Gly |
| GTA | Val | GCA | Ala | GAA | Glu | GGA | Gly |
| GTG | Val | GCG | Ala | GAG | Glu | GGG | Gly |

*When residing within a coding sequence

In addition, those of ordinary skill in the art will recognize that such degenerate codons further include RNA sequences, wherein uracil ("U") replaces thymine ("T"). For purposes of illustration, SEQ ID NO: 100 and SEQ ID NO: 101 represent examples of nucleic acid sequences that encode Peptide 1 (SEQ ID NO: 1) and Peptide 2 (SEQ ID NO: 2), respectively.

The expression systems that may be used to produce the peptide vaccines of the invention include, without limitation, microorganisms such as bacteria (e.g., *E. coli, B. subtilis*) transformed with recombinant bacteriophage DNA, plasmid DNA, or cosmid DNA expression vectors containing peptide vaccine-encoding nucleotide sequences; yeast (e.g., *Saccharomyces, Pichia*) transformed with recombinant yeast expression vectors containing peptide vaccine-encoding nucleotide sequences; insect cell systems infected with recombinant virus expression vectors (e.g., baculovirus) containing peptide vaccine-encoding sequences; plant cell systems infected with recombinant virus expression vectors (e.g., cauliflower mosaic virus, CaMV; tobacco mosaic virus, TMV; cowpea mosaic virus, CPMV) or transformed with recombinant plasmid expression vectors (e.g., the Ti plasmid) containing peptide vaccine-encoding nucleotide sequences; or mammalian cell systems (e.g., COS, CHO, BHK, 293, 3T3) harboring recombinant expression constructs containing peptide vaccine-encoding sequences operably linked to promoters derived from the genome of mammalian cells (e.g., metallothionein promoter) or from mammalian viruses (e.g., the adenovirus late promoter; the vaccinia virus 7.5K promoter; or others).

In bacterial systems, for example, a number of expression vectors may be employed. In certain embodiments, for example, vectors that direct the expression of high levels of fusion protein products (which are easily purified) may be desirable. Such vectors include, without limitation, the *E. coli* expression vector pUR278 (Ruther et al. (1983) *EMBO J.* 2:1791), in which a peptide vaccine-encoding sequence may be ligated into the vector in frame with a lacZ coding region, wherein a fusion protein is produced; pIN vectors (Inouye and Inouye (1985) *Nucleic Acids Res.* 13:3101-3109; Van Heeke and Schuster (1989) *J. Biol. Chem.* 264:5503-5509); and the like.

pGEX vectors may also be used to express peptide vaccines as fusion proteins with glutathione S-transferase (GST). In general, such fusion proteins are soluble and may be easily purified from lysed cells by adsorption to glutathione-agarose beads followed by elution in the presence of free glutathione. The pGEX vectors are, preferably, designed to include thrombin or factor Xa protease cleavage sites to allow the peptide vaccine to be released from the GST moiety.

In an insect system, for example, *Autographa californica* nuclear polyhidrosis virus (AcNPV) may be used as a vector to express peptide vaccine-encoding nucleotides. The virus may be cultured in *Spodoptera frugiperda* cells. A peptide vaccine-encoding polynucleotide sequence, for example, may be cloned into non-essential regions (for example the polyhedrin gene) of the virus and placed under control of an AcNPV promoter (for example the polyhedrin promoter). Successful insertion of the peptide vaccine-encoding sequence will, preferably, inactivate the polyhedrin gene and production of non-occluded recombinant virus (i.e., virus lacking the proteinaceous coat—encoded by the polyhedrin gene). Such recombinant viruses may then be used to infect *Spodoptera frugiperda* cells in which the inserted polynucleotide sequence is expressed (See, e.g., Smith et al. (1983) *J. Virol.* 46: 584; and Smith, U.S. Pat. No. 4,215,051).

In mammalian host cells, for example, a number of viral-based expression systems may be utilized. For example, an adenovirus may be used as an expression vector, wherein the peptide vaccine-encoding nucleotide sequence of interest may be ligated to an adenovirus transcription/translation control complex, e.g., the late promoter and tripartite leader sequence. The resulting chimeric sequence may then be inserted into the adenovirus genome using in vitro or in vivo recombination. Insertion into a non-essential region of the viral genome (e.g., region E1 or E3), preferably, results in a recombinant virus capable of expressing a peptide vaccine in infected hosts (See, e.g., Logan and Shenk (1984) *Proc. Natl. Acad. Sci. USA* 81:3655-3659).

Still further, the invention contemplates that the peptide vaccines may be conjugated to, associated with, or expressed on the surface of certain immunogenic plant viruses, such as tobacco mosaic virus (TMV) (Koo, M., et. al. (1999) Protective immunity against murine hepatitis virus (MHV) induced by intranasal or subcutaneous administration of hybrids of tobacco mosaic virus that carries an MHV epitope. *Proc. Natl. Acad. Sci., USA* 96:7774-79) and cowpea mosaic virus (CPMV) (Usha R., et al. (1993) Expression of an animal virus antigenic site on the surface of a plant virus particle. *Virology* 197:366-74). Indeed, plant viruses offer several advantages for the production of peptide vaccines, such as eliminating the risks associated with using animal pathogens during production, relative ease of genetic manipulation, and economical production. In certain embodiments, for example, a peptide vaccine may be expressed as a fusion protein with plant virus coat proteins, wherein such coat proteins function as carrier molecules. In such embodiments, the coat proteins may self-assemble and form recombinant virus particles displaying the desired peptide vaccine on their surfaces. The coat protein of tobacco mosaic virus (TMV) was among the first plant virus proteins to be used as a carrier molecule for antigenic epitopes from other sources. See Fitchen, J., Beachy, R. N. & Hein, M. B. (1995) *Vaccine* 13, 1051-57; and McLain, L., Porta, C., Lomonossoff, G. P., Durrani, Z. & Dimmock, N. J. (1995) *AIDS Res. Hum. Retroviruses* 11, 327-34. In certain embodiments, for example, a peptide vaccine-encoding sequence may be fused with the coding sequence of a TMV coat protein and cloned into an appropriate vector for expression in virus-infected plants. Virus particles expressing the peptide vaccine may then be purified from infected plant tissue and used to immunize an immunocompetent subject—resulting in a humoral immune response to such peptide vaccine. See also Sugiyama, Hamamoto, Takemoto, Watanabe, Okada (1995) "Systematic Production of Foreign Peptides on the Particle Surface of Tobacco Mosaic Virus," *FEBS Lett.* 359:247-250.

Those of ordinary skill in the art will appreciate that specific initiation signals may be required for efficient translation of peptide vaccine-encoding nucleotide sequences. Non-limiting examples of such signals include the ATG initiation codon and adjacent sequences. More particularly, when the peptide vaccine-encoding sequence comprises an initiation codon (and other necessary control sequences) and is inserted into an appropriate expression vector, no additional translational control signals may be needed. Of course, when such peptide vaccine-encoding sequences do not comprise such control sequences, certain exogenous transcriptional/translational control signals must be provided, including without limitation the ATG initiation codon, enhancer elements, transcription terminators, and/or others known in the art. Such exogenous transcriptional/translational control signals and initiation codons may be of a variety of origins, both native and non-native. Furthermore, those skilled in the art will appreciate that the initiation codon must be in phase with the reading frame of the desired peptide vaccine-encoding sequence to ensure transcription and translation of the entire coding region.

In other embodiments, a host cell strain may be chosen that modulates the expression of the peptide vaccine-encoding sequences, or modifies and processes the gene product in a specific fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems may be selected to impart the desired modification and processing on the expressed peptide vaccine.

In still other embodiments, as suggested above, the peptide vaccines may be expressed as fusion proteins, which may be readily purified using, for example, an antibody specific for the fusion protein. For example, a system described by Janknecht et al. allows for the efficient purification of non-denatured fusion proteins expressed in human cell lines (Janknecht, et al. (1991) *Proc. Natl. Acad. Sci. USA* 88:8972-76).

In such example, the polynucleotide of interest, e.g., a peptide vaccine-encoding sequence, is subcloned into a vaccinia recombination plasmid, wherein the open reading frame of such polynucleotide is translationally fused to an amino-terminal tag consisting of six histidine residues. Extracts from cells infected with such recombinant vaccinia virus are loaded onto $Ni^{2+}$ nitriloacetic acid-agarose columns and histidine-tagged proteins are selectively eluted with imidazole-containing buffers.

While the expression systems described above (and others), for example, may be used to produce the peptide vaccines contemplated by the present invention, in other embodiments, the vaccines may be chemically synthesized. Such chemical synthesis may be conducted using any method known in art, such as either F-moc (9-fluorenylmethyloxy-carbonyl) chemistry, essentially as described by D. Hudson (1988) or Boc (tert-butyloxycarbonoyl) chemistry. Techniques for amino acid synthesis are routinely employed by those of ordinary skill in the art using currently available laboratory equipment (e.g., Applied Biosystems, Inc., Foster City, Calif.).

Following chemical synthesis, peptides are generally purified using high pressure liquid chromatography (HPLC), and the integrity and authenticity of the peptides are determined by limited Edman degradation followed by traditional sequencing such as mass-spectrophotometric analyses and NMR analysis of the intact peptide. In addition, the synthetically produced peptide vaccines are, preferably, analyzed for biological activity using any of numerous in vitro assays known in the art—examples of which are described below.

The peptide vaccines of the present invention may, optionally, be conjugated, linked, or otherwise associated with one or more carrier molecules, such as keyhole limpet hemocyanin (KLH), bovine serum albumin (BSA), or others well known in the art. The peptide vaccines may be conjugated to such carrier molecules using any suitable means. For example, the peptide vaccines may be conjugated to such carrier molecules via disulfide bonding, as described in, for example, Bernatowicz et al. (1986) *Anal. Biochem.* 155:95-102. Other carrier molecules suitable for conjugation with the peptide vaccine of the present invention may include, for example, sheep albumin, *E. coli* pilin protein k99, rotavirus VP6 protein, polysaccharides such as mannan, and various lipopolysaccharides such as those derived from *Salmonella typhosa*.

Still further, the peptide vaccines of the present invention may be, optionally, associated with certain adjuvants well known in the art. For example, such peptide vaccines may be emulsified in Freunds adjuvant (complete or incomplete) or MPL-TDM adjuvant (monophosphoryl Lipid A, synthetic trehalose dicorynomycolate)—prior to administering to an immunocompetent subject.

In Vitro Testing

Following the production of a peptide vaccine of the present invention, the vaccine is, preferably, tested and screened for efficacy using any of the numerous in vitro diagnostics which are readily available and known in the art. In general, for example, the effectiveness of the peptide vaccines of the present invention may be tested by measuring IgG antibody titers to the peptide vaccine, IgG antibody titers to native forms of the target capsid proteins, the ability of such antibody to inhibit pathogen infection in a neutralization assay, and other tests and diagnostics.

After designing a peptide vaccine of the present invention, antibodies may be generated for in vitro analysis. The methods by which such antibodies may be generated are well known to those of ordinary skill in the art. For example, such antibodies may be raised by immunizing any of various host animals by innoculation with a suitable amount of such peptide vaccine and, following immunization, collecting antisera from such host animals. The host animals which may be employed include, without limitation, pigs, rabbits, chickens, mice, goats, rats, and others commonly used in the art. Various adjuvants may also be used to increase the immune response of the host animal, including, for example, Freund's adjuvant (complete and incomplete), mineral salts such as aluminum hydroxide or aluminum phosphate, surface active substances such as lysolecithin, pluronic polyols, polyanions, peptides, oil emulsions, and others known in the art. In other cases, as mentioned above, the immune response may be enhanced by administering the peptide vaccine to the host animal in combination with (or conjugated to) the carrier molecules described herein.

After immunization, the host animal is generally bled to retrieve the desired antisera. Preferably, the initial bleed is purified using methods well known in the art. For example, the polyclonal antiserum may be subjected to a caprylic acid precipitation procedure in order to remove the majority of extraneous serum proteins, such as albumins. An ammonium sulphate precipitation may then be conducted to provide an immunoglobulin enriched fraction. At this stage of purification, the antisera may be sufficiently pure for in vitro studies.

If further purification is necessary or desired, however, the immunoglobulin fraction may be subjected to affinity chromatography. For example, the fraction may be applied to a chromatographic column on which Protein A, G and/or L are immobilized. When carried out under optimal conditions, such affinity chromatography steps may provide highly purified and concentrated immunoglobulins.

After obtaining the desired fraction of antisera, the potential effectiveness of the peptide vaccine may be initially assessed by, for example, determining the IgG antibody titer to the vaccine itself. In addition, for example, the IgG antibody titers to the native form of the target capsid proteins may be measured. Still further, the ability of such antibody to inhibit viral infection is preferably assessed using, for example, any readily available neutralization assay.

IgG titers to the peptide vaccine may be determined using, for example, a standard enzyme-linked immunosorbent assay (ELISA). In short, any commercially-available microtiter plate may be coated with the peptide vaccine at sufficient concentrations (which may vary depending on the vaccine composition and ELISA system employed), such as 0.5, 1.0, 2.0, or 3.0 µg/mL in phosphate-buffered saline (PBS). After incubation, the coating solution is removed and unbound sites are blocked by the addition of, for example, 2% (w/v) powdered skim milk. Preferably, the plate is subsequently washed three times with PBS containing 0.02% Tween 20 to remove any free peptide.

Serial dilutions of the antisera described above are generated and subsequently added to the peptide vaccine-coated microtiter plate and incubated, wherein each dilution is added to separate wells (or a separate series of wells). Following binding of the antisera dilutions, unbound antibodies may be removed by, for example, washing the plate with PBS as described above. Next, a secondary anti-(host animal) IgG antibody (an antibody coupled to, for example, an enzyme that may be used to generate a signal that may be quantified using photometric methods) may be added to the microtiter plate, incubated, and subsequently washed as described above to remove unbound antibody. Of course, the secondary antibody should recognize and bind to an IgG raised in the host animal which is used to produce the antisera (against the peptide vaccine) described above. The amount of bound secondary antibody may be measured using spectrophotometric readings following the addition of a chromogenic or fluorescent substrate (the identity and concentration of which will depend on, among other variables, the enzyme which is coupled to the secondary antibody).

In general, the potential effectiveness of the tested peptide vaccine may be indirectly assessed by measuring the relative titer of the antisera using, for example, the general assay outlined above (or any of the other assays well known in the art). More specifically, the higher the relative titer, the greater the potential that such peptide vaccine may elicit a desirable immune response in a subject. In general, the titer of such antisera is the last dilution which results in a spectrophotometric reading (e.g., produces an optical density) which is above the background reading (or exceeds the background reading by a defined amount). The background reading may be represented by, for example, microtiter wells that receive the peptide vaccine, blocking agent and secondary antibody (but which do not receive the test antisera).

Thus, for example, a first antisera which may be diluted to a final concentration of 1:200 and still produce spectrophotometric readings that significantly exceed background readings exhibits a higher "titer" than a second antisera which may only be diluted to 1:50 to achieve the same results. In general, it follows that the peptide vaccine which yielded the first antisera may have relatively more potential as an effective vaccine than the peptide which yielded the second antisera. Those of ordinary skill in the art will appreciate that the above example is overly simplistic, and that numerous other variables may affect antisera titer, such as variation between host animals, environmental factors, and numerous others. Thus, such in vitro analyses are, preferably, used to generally identify and screen the peptide vaccines which should be investigated further.

IgG titers to the target capsid proteins are similarly determined, except that the native capsid protein is used to initially coat the microtiter plate wells. Because some fractions of native protein denature upon contact with plastic (i.e., the microtiter plate), an alternative competitive binding assay may be conducted. Such competitive binding assays are commonly performed by those of ordinary skill in the art.

Preferably, the peptide vaccines are further tested for the ability to elicit a preferred immune response using a neutralization assay. For example, plaque assays may be performed as previously described (Shepard, Heinz, et al. (1993) *J. Virol.* 67: 2245-54). Briefly, $1.4 \times 10^6$ HeLa cells in 5 mL of AH medium (supplemented with 10% bovine serum) may be layered on 60 mm cell culture plates and incubated at 35° C. for 8-10 hours until monolayers form. The monolayers are preferably washed with PBS prior to infection. Virus samples are mixed with serial dilutions of test antisera/antibodies (which are generated against the test peptide vaccine(s) as described above) and then added to the monolayer and allowed to attach for 1 hour at room temperature. The monolayers are then washed with PBS and overlayed with 2.5 mL of P6 media mixed with 0.8% agar and then topped with 2.5 mL of P6 media. The plates are subsequently incubated at 35° C. under 5% $CO_2$ for 48 hours and then stained with crystal violet for plaque forming units (PFU) determination.

The invention further contemplates that the treatment efficacy potential of a peptide vaccine may be measured in a patient, i.e., an immunocompetent subject. The term "treatment efficacy potential," as used herein, relative to treatment and/or prevention of rhinovirus infection, for example, refers to the potential effectiveness of a given peptide vaccine (which is administered using a standard treatment strategy) to elicit a desired immune response (and/or to modulate certain other patient symptoms), as determined by evaluation of various clinical endpoints.

The evaluation of various clinical endpoints may include, for example, measuring the relative titer of antibodies (which may be taken from any suitable body fluid) which the subject generates after immunization with a peptide vaccine of the invention. The relative titer of such antibodies may be determined using the assays contemplated herein (or any other suitable diagnostic). The term "body fluid" may include, for example, urine, saliva, plasma, blood, spinal fluid, and other samples of biological origin. Such evaluation relative to the immune response may be quantitative (e.g., measuring the titer referenced above) or qualitative (e.g., assessing whether subjects provided with one or more peptide vaccines are effectively immunized from the viral targets—using standard medical protocols).

Vaccine Compositions

The vaccine compositions of the present invention that are administered to a subject, preferably, include (i) an effective amount of the peptide vaccine, which may include carrier molecules and/or adjuvants, and, optionally, (ii) preservatives, buffers, and the like. Descriptions of vaccine formulations may be found in Voller, A. et al., New Trends and Developments in Vaccines, University Park Press, Baltimore, Md. (1978).

In certain preferred embodiments, the peptide vaccines that may be used to formulate a finished vaccine composition of the present invention, which may be administered to a subject, are in a substantially isolated and purified form. For example, in certain preferred embodiments, such vaccine compositions may be formulated by adding a substantially isolated and purified form of a peptide vaccine to an adjuvant, buffer, or other compositions suitable for administration to a subject. In certain preferred embodiments, for example, such peptide vaccines may be substantially isolated and purified forms of a protein comprising SEQ ID NO:1, a protein comprising SEQ ID NO:2, a protein comprising an amino acid sequence that is functionally equivalent to SEQ ID NO:1 or SEQ ID NO:2, or any combination of the foregoing.

Subject Applications

The peptide vaccines of the present invention may be administered using any method generally understood in the art. In many cases, currently-available vaccines are administered systemically by injection. The invention provides, however, that any other effective means of administration may be employed (currently existing or discovered hereafter). Still further, for example, with suitable formulation, peptide vaccines may be administered across the mucus membrane using penetrants, such as bile salts or fusidic acids—typically in combination with a surfactant. In still other applications, peptide vaccines may be administered using transcutaneous methods or, in some cases, using oral formulations.

Dosage levels depend on the mode of administration, the nature of the subject, and, if applicable, the composition of the carrier/adjuvant formulation used. In many cases, however, it is envisaged that an effective amount of the peptide vaccine may range between about 0.01 µg/kg-1.00 mg/kg body weight. In certain embodiments, successively spaced administrations of the peptide vaccine may be employed in the immunization protocol, as is often standard in the art. The term "successively spaced administrations," as used herein, refers to treatment regimens of one or more of the peptide vaccines of the present invention, which comprise an initial administration, followed by one or more "booster" administrations at various time intervals following the initial administration. The "booster" administrations may or may not be given at regularly spaced intervals.

The present invention may further draw upon the value and potential of antibodies for in vivo therapy, which has been long-recognized in the art. More specifically, the invention contemplates that the peptide vaccines of the present invention may be used to generate antibodies (polyclonal and/or monoclonal antibodies) for use in passive immunization. The term "passive immunization," as used herein, refers to the direct administration of antibodies to a subject as an immunization approach and/or to treat an existing infection. For example, the invention contemplates that one or more peptide vaccines of the present invention may be used to generate antibodies against such peptide (and, in accordance with the present invention, the corresponding transiently exposed and genetically conserved capsid proteins), wherein such antibodies may be subsequently administered to subjects. It is envisaged that such passive immunization techniques may be used to prevent or treat viral infections.

In still further embodiments, for example, the present invention may be used to produce antibodies (either polyclonal or monoclonal) for topical administration. For purposes of illustration, the invention contemplates that such topical administrations may be used, in some cases, as anti-rabies compositions to treat a wound area (which may prevent systemic infection by the virus). In any of the foregoing passive immunization or therapeutic embodiments, such antibodies may be adapted using methods well known in the art to render them more tolerable to the host immune system. With respect to human therapeutics, for example, such adaptations are commonly referred to as "humanizing" the antibodies. In this way, it is possible to create antibodies to the target peptide, which may be administered topically or intravenously, which do not elicit a subject immune response that destroys the therapeutic antibodies.

The following Examples are included to demonstrate certain embodiments of the invention. It should be appreciated by those skilled in the art that the techniques disclosed in the Examples that follow represent techniques discovered by the inventor to function well in the practice of the invention, and thus, may be considered to constitute preferred modes for its practice. However, those of ordinary skill in the art should, in light of the present disclosure, appreciate that many changes may be made in the specific embodiments that are disclosed and still obtain a like or similar result without departing from the spirit and scope of the invention.

EXAMPLES

The N-termini of VP4 capsid proteins are transiently exposed on the surface of the human rhinovirus. Unlike the virion surface, the N-termini of VP4 capsid proteins are extremely well conserved among the various rhinovirus serotypes. Furthermore, x-ray crystallographic studies suggest that the nature of the extrusion (not shown herein) is likely to present a linear, peptide-like conformation of the termini to the outer surface. Accordingly, the invention contemplates that a peptide representing (or functionally equivalent to) the N-termini of VP4 capsid proteins may be used as a pan-serotype vaccine. In the following Examples, certain transiently exposed portions of the N-termini of VP4 capsid proteins were used to demonstrate such embodiments of the present invention.

Example 1

MALDI Analysis of the VP4 Capsid Protein

Human rhinovirus was produced using previously described protocols (Erickson, Frankenberger et al. (1983) *Proc. Natl. Acad. Sci. USA* 80: 9314). In brief, HeLa cells were infected with HRV14 at a multiplicity of infection of 10. After incubating the infected cells at 35° C. for 9-10 hours, the virus was purified from lysed cells treated with N-lauryl-sarcosine to solubilize cellular debris. However, unlike the previously described protocols, the lysed cellular material was not treated with trypsin since even this brief treatment resulted in cleavage of VP1 and VP4 (Lewis, Bothner et al. (1998) *Proc. Natl. Acad. Sci.* 95:6774-78). Virus particles were pelleted by ultracentrifugation at 280 Kg for 2 hours. The virus was then resuspended in 20 mM Tris buffer, pH 7.6, and further purified using 7.5-45% sucrose gradients centrifuged at $2 \times 10^5$ g for 1.5 hours. The virus bands were collected, pooled and dialyzed overnight at 4° C. against 20 mM Tris buffer, pH 7.2. HRV14 concentration was determined spectrophotometrically using an extinction coefficient of 7.7 ml/mg-cm at 260 nm and stored at 4° C.

Limited proteolytic digestions of purified HRV14 were performed at 37° C. Modified trypsin (Promega, Madison, Wis.) and Glu-C (Roche Diagnostics, Indianapolis, Ind.) digests were performed in 10 mM ammonium bicarbonate, pH 7.8. Trypsin to virus ratios of 1:500 and 1:1000 (w/w) were used for these limited proteolysis experiments. The digested HRV14 particles were then subjected to mass spectrophotometry analysis.

Qualitative mass spectrometry experiments were conducted using a PerSeptive Biosystems (Framingham, Mass.) Voyager-DE™ STR MALDI time-of-flight reflectron mass spectrometer equipped with a nitrogen laser. MALDI generated ions were accelerated into the time-of-flight mass analyzer by a 20 kV pulse after a 200 ns delayed extraction period. Detector voltages were turned on after ions greater than m/z 600 had passed the detector (with a "low mass gate") to improve detection sensitivity for the ions of interest. MALDI analyses utilized 3,5-hydroxycinnamic acid (Sigma-Aldrich, St. Louis, Mo.) as the matrix dissolved in a 70% acetonitrile/30% water (0.1% trifluoroacetic acid) solution. Sample volumes of 0.5 µL were applied to the MALDI plate followed by 0.5 µL of the matrix solution and allowed to dry. All MALDI spectra were generated from an average of 128 laser pulses.

The results of mass spectroscopic analysis of the products of trypsin digestion of HRV14 demonstrated that there are significant capsid dynamics in rhinoviruses. In particular, trypsin was found to cleave HRV14 adjacent to the highly exposed, exterior NIm-IA site. However, trypsin also cleaved the VP1 and VP4 amino termini that lie buried at the capsid/RNA interface. Use of immobilized trypsin provided similar results and demonstrated that cleavage of buried residues cannot be attributed to penetration of the capsid by trypsin and therefore demonstrated that the buried N-termini are being extruded from the virions.

As a control, the trypsin digestion experiments were also performed in the presence of antiviral WIN compounds. WIN compounds, that are known to stabilize the capsid structure, completely block cleavage at all of the sites. The capsid protein of HRV14 alone is cleaved by trypsin within five minutes, whereas the presence of WIN compounds delays cleavage for more than 18 hours. These experiments demonstrated that trypsin did not cleave the capsid proteins by penetrating the capsid and, furthermore, that the cleavage is not due to particles damaged during purification since there was such a profound effect of the WIN compounds on trypsinolysis.

Example 2

Determination of the Vaccine Target

The amino acid sequence of portions of the N-termini of the VP4 capsid proteins (for 97 different human rhinovirus serotypes) were analyzed to identify areas of preferred sequence conservation. The 97 different VP4 amino acid sequences were aligned and compared using BLAST. After conducting such analysis, two groups of homologous (i.e., conserved) sequences were apparent.

More specifically, it was found that preferred sequence conservation existed within two subsets of serotypes. SEQ ID NO 3-27 represents a first group of amino acid sequences which exist on transiently exposed portions of the N-termini of VP4 capsid proteins (referred to herein as "HRV Group 1"). SEQ ID NO 28-99 represents a second group of amino acid sequences which exist on transiently exposed portions of the N-termini of VP4 capsid proteins (referred to herein as "HRV Group 2").

While such groups of preferred sequence conservation were identified electronically using the above software program, the remarkable sequence conservation within each of HRV Group 1 and HRV Group 2 may be visually appreciated by a brief review of FIGS. 1 and 2, respectively. In addition, FIG. 3 shows that VP4 is highly conserved relative to other capsid proteins (e.g., VP1)—and that such conservation is not wholly correlated to whether a particular region of such capsid protein is externally exposed. This suggests that the function of VP4 may force it to be more highly conserved than other buried regions of the capsid. Accordingly, it will be appreciated that such conservation will reduce the risk that such portions of VP4 proteins could undergo "escape" mutations, which could eliminate the effectiveness of a peptide vaccine of the present invention (making the VP4 protein of the rhinovirus capsid a unique and excellent vaccine target).

FIG. 3 further shows that a substantial portion VP1 is buried within the capsid (and therefore hidden from the immune system). Such VP1 residues, however, do not exhibit the same high level of conservation as VP4.

Moreover, while the sequence conservation was divided between HRV Group 1 and HRV Group 2 in this Example (prior to designing non-limiting examples of peptide vaccines of the present invention), it should further be appreciated that a certain level of conservation exists at such locations of the VP4 protein across all 97 serotypes analyzed (without segregating the serotypes into HRV Groups 1 and 2). The invention therefore provides that peptide vaccines may also be designed based on such transiently exposed regions of the VP4 protein, without segregating the serotypes into two or more groups.

In certain embodiments, amino acid sequences of such VP4 regions which may be statistical outliers, i.e., which represent confined deviations from the overall homology exhibited among certain locations of VP4 capsid proteins, may be excluded from consideration when designing a peptide vaccine of the current invention. Referring to FIG. 4, for example, 9 amino acid sequences are shown which represent portions of transiently exposed regions of VP4 capsid proteins from 9 different rhinovirus serotypes. As shown, remarkable conservation exists at such location among 8 of 9 such serotypes, while only 1 serotype exhibits less than preferred conservation ("Rhino14"). Thus, the invention contemplates that a peptide vaccine may be designed based on, for example, the conserved sequences among such 8 of 9 serotypes (while excluding the sequence of "Rhino14" from consideration when designing the peptide vaccine).

Example 3

Peptide Vaccine Design

After identifying the two groups of preferred sequence conservation described above (HRV Groups 1 and 2), peptide vaccines were designed. As discussed herein, a first peptide vaccine was designed to represent a functionally equivalent peptide of the sequences comprising HRV Group 1 (referred to herein as "Peptide Vaccine 1") (SEQ ID NO 1). Peptide Vaccine 1 represents a native sequence of the N-termini of the human rhinovirus 14 VP4 capsid proteins. In addition, a second peptide vaccine was designed to represent a functionally equivalent peptide of the sequences comprising HRV Group 2 (referred to herein as "Peptide Vaccine 2") (SEQ ID NO 2).

FIG. 5 shows a graphical representation of Peptide Vaccines 1 and 2. The sequences illustrated therein are annotated to show the degree of conservation within each of the two groups, namely, HRV Groups 1 and 2. In this Example, the degree of conservation was measured by percentage identity for each residue comprising Peptide Vaccines 1 and 2. For example, with respect to Peptide Vaccine 1, the percent identity for each residue was calculated by dividing the number of serotypes which include the same residue as Peptide Vaccine 1 at the same location by 27 (i.e., the total number of serotypes represented by HRV Group 1). Similar analysis was conducted for Peptide Vaccine 2 relative to HRV Group 2. As discussed herein, in addition to percent identity, other biological factors may be considered in designing such functionally equivalent peptide vaccines.

Of course, administering the vaccines represented by Peptide Vaccine 1 and Peptide Vaccine 2 to an immunocompetent subject would, preferably, elicit an immune response which would be effective against the various regions of VP4 comprising HRV Groups 1 and 2, respectively.

Example 4

Production of Antibodies for In Vitro Analysis

Antibodies were raised against Peptide Vaccines 1 and 2. The different peptides used for immunization included a peptide representing HRV14 VP4, with its N-terminus unmyristoylated (Peptide Vaccine 1), and one with its N-terminus myristoylated (Peptide Vaccine 2). The polyclonal antibodies raised against Peptide Vaccines 1 and 2 were produced by the Synpep Corporation (Dublin, Calif.) and Sigma Genosys (TE Woodlands, Tex.), respectively.

In short, both unmyristoylated and myristoylated peptide synthesis were performed using standard t-butyloxycarbonyl chemistry. The peptides were conjugated with keyhole lymphocyte (KLH) using EDC (1-Ethyl-3-(3-Dimethylamino-propyl)carbodiimide Hydrochloride) as a cross linker. The peptides were HPLC purified to ~70% purity prior to injection. Polyclonal antibodies were produced by injecting New Zealand white rabbits with 200 μg of the subject peptide vaccine (contained within complete Freund's adjuvant), followed by multiple booster injections every two weeks for two months (which comprised 100 μg of the peptide vaccine in incomplete Freund's adjuvant). Serum samples were collected every two weeks beginning 49 days after the first injection.

Example 5

In Vitro Analysis of the Peptide Vaccines

Human rhinovirus was produced as described in Example 1. The Wisconsin-HeLa (WI-HeLa) cell line was passaged in suspension culture in medium B (suspension-Minimum essential medium: Sigma) supplemented with 10% bovine serum (Gibco, Invitrogen Corporation, Carlsbad, Calif.). Virus stocks for HRV14 have been described elsewhere (Shepard, Heinz et al. (1993) J. Virol. 67: 2245-54). HRV16 stocks were prepared from HRV16 cDNA (Lee and Wang (2003) *J. Virol.* 77: 6235-44). HRV3 and HRV29 serotypes were obtained from the American Type Culture Collection (ATCC) and were further amplified using HeLa cell monolayers. Neutralization (plaque) assays were performed as described herein.

As shown in FIG. 6, and consistent with the MALDI results, antibodies raised against Peptide Vaccine 1 (also referred to herein as "anti-HRV14 antibodies") are effective in blocking human rhinovirus 14 (HRV14) infectivity. In addition, FIG. 6 shows that such activity is time-dependent. For example, referring to the 0.200 dilution, 8 hours of incubation with anti-HRV14 antibodies was shown to impact rhinovirus viability significantly more than 1 hour of incubation. A similar trend is shown for the 0.100 dilution. Still further, FIG. 6 shows that the concentration of such antibodies impacts activity. For example, following 1 hour and 8 hours of incubation, the 0.200 dilution impacted HRV14 viability significantly more than the 0.100 dilution.

Figure 7:
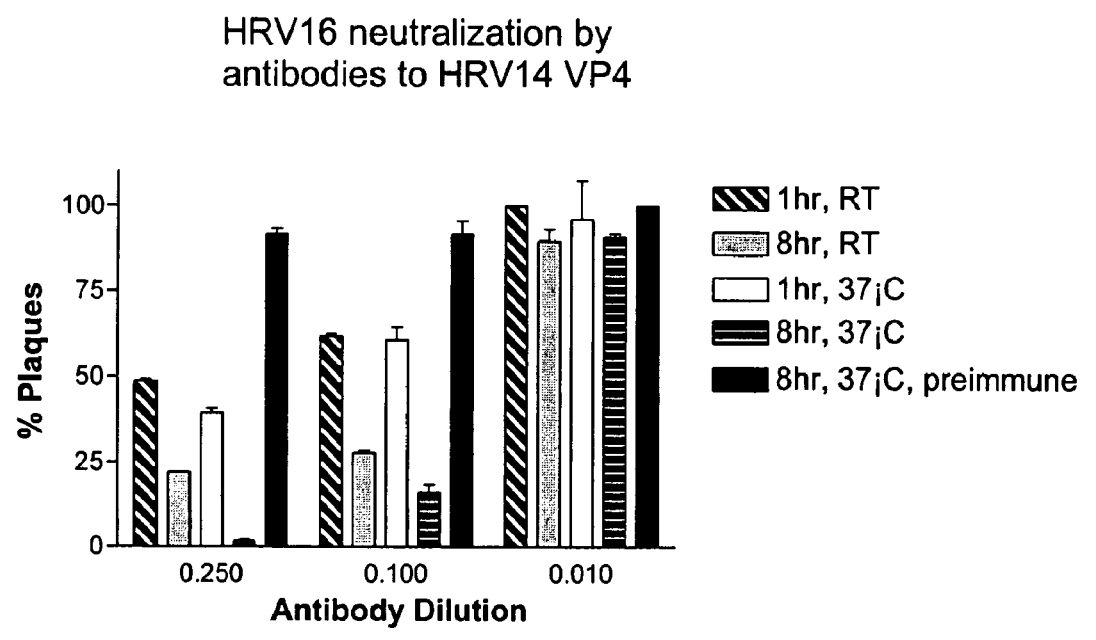

The antibodies raised against Peptide Vaccine 1 were further shown to impact rhinovirus viability in other serotypes (i.e., other than HRV14). Referring to FIG. 7, for example, such antibodies (raised against Peptide Vaccine 1) were shown to negatively impact the viability of human rhinovirus 16 (HRV16). Referring to FIG. 7, the time-dependent and concentration-dependent activity of the anti-Peptide Vaccine 1 antibodies (described above) was also observed against HRV16. In addition, as shown in FIG. 7, the anti-Peptide Vaccine 1 activity may be influenced by temperature. Such temperature-dependency was found to be consistent with the MALDI results, which demonstrated that the "breathing" process of the HRV16 capsid is a temperature-dependent phenomenon (data not shown).

Referring to FIG. 8, antibodies raised against Peptide Vaccine 1 were further shown to negatively impact the viability of human rhinovirus 29 (HRV29). This represents the first time that a peptide has been used to induce pan-serotypic neutralizing antibodies against human rhinovirus.

As discussed above, antibodies were also raised against Peptide Vaccine 2 (SEQ ID NO 2). As shown in FIG. 9, the results demonstrate that antibodies raised against Peptide Vaccine 2 also exhibit pan-serotypic neutralization. Specifically, the antibodies were shown to negatively affect the infectivity of human rhinovirus 14. Thus, the foregoing data show that both peptides, i.e., Peptide Vaccines 1 and 2, are capable of eliciting an immune response (or inducing the production of polyclonal serum) with pan-serotypic activity.

In contrast, it should be noted that antibodies were also raised against the first 25 amino acid residues of the N-termini of VP1 capsid proteins of HRV14, a substantial portion of which are buried within the capsid, but which do not exhibit the same high level of conservation as VP4 (as mentioned above). Importantly, such portions of the VP1 capsid proteins did not elicit polyclonal serum with pan-serotypic activity and, moreover, were not able to neutralize HRV14 replication (data not shown). Accordingly, the foregoing shows that the N-termini of VP4 capsid proteins in rhinoviruses constitute unique and suitable targets for peptide vaccines of the present invention.

Those of ordinary skill in the art will appreciate the significant impact of the inventions described herein. The Examples described herein represent the first time that a single peptide vaccine has been shown to produce antibodies which are capable of neutralizing multiple serotypes of human rhinoviruses. In addition, the foregoing represents the first example of a linear epitope being useful in generating neutralizing antibodies against human rhinoviruses.

The many aspects and benefits of the invention are apparent from the detailed description, and thus, it is intended for the following claims to cover all such aspects and benefits of the invention which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

REFERENCES

Bothner, B., A. Schneemann, D. Marshall, V. Reddy, J. E. Johnson and G. Siuzdak (1999). "Crystallographically Identical Virus Capsids Display Different Properties in Solution." Nature Struc. Blol. 6: 114-116.

Colonno, R. J., J. H. Condra, S. Mizutani, P. L. Callahan, M. E. Davies and M. A. Murcko (1988). "Evidence for the direct involvement of the rhinovirus canyon in receptor binding." Proc. Natl. Acad. Sci. USA 85: 5449-5453.

Fricks, C. E. and J. M. Hogle (1990). "Cell-induced conformational change in poliovirus: externalization of the amino terminus of VP1 is responsible for liposome binding." J. Virol. 64: 1934-1945.

Kolatkar, P. R., J. Bella, N. H. Olson, C. M. Bator, T. S. Baker and M. G. Rossmann (1999). "Structural studies of two rhinovirus serotypes complexed with fragments of their cellular receptor." EMBO J. 18: 6249-6259.

Lee, W.-M. Wang, W. (2003). "Human Rhinovirus Type 16: Mutant V1210A requires capsid-binding drug for assembly of pentamers to form virions during morphogenesis." J. Virol. 77: 6235-6244.

Lewis, J. K., B. Bothner, T. J. Smith and G. Siuzdak (1998). "Antiviral agent blocks breathing of the common cold virus." Proc. Natl. Acad. Sci. USA 95: 6774-6778.

Li, Q., A. G. Yafal, Y. M. H. Lee, J. Hogle and M. Chow (1994). "Poliovirus neutralization by antibodies to internal epitopes of VP4 and VP1 results from reversible exposure of the sequences at physiological temperatures." J. Virol. 68: 3965-3970.

Olson, N. H., P. R. Kolatkar, M. A. Oliveira, R. H. Cheng, J. M. Greve, A. McClelland, T. S. Baker and M. G. Rossmann (1993). "Structure of a human rhinovirus complexed with its receptor molecule." Proc. Natl. Acad. Sci. USA 90: 507-511.

Rossmann, M. G., E. Arnold, J. W. Erickson, E. A. Frankenberger, J. P. Griffith, H. J. Hecht, J. E. Johnson, G. Kamer, M. Luo, A. G. Mosser, R. R. Rueckert, B. Sherry and G. Vriend (1985). "Structure of a human common cold virus and functional relationship to other picornaviruses." Nature (London) 317: 145-153.

Rueckert, R. R. (1996). Picornaviridae and their replication. New York, Raven Press. Shepard, D. A., B. A. Heinz, et al. (1993). "WIN 52035-2 inhibits both attachment and eclipse of human rhinovirus 14." J. Virol. 67: 2245-2254.

Sherry, B., A. G. Mosser, R. J. Colonno and R. R. Rueckert (1986). "Use of monoclonal antibodies to identify four neutralization immunogens on a common cold picornavirus, human rhinovirus 14." J. Virol. 57: 246-257.

Sherry, B. and R. R. Rueckert (1985). "Evidence for at least two dominant neutralization antigens on human rhinovirus 14." J. Virol. 53: 137-143.

Smith, T. J., M. J. Kremer, M. Luo, G. Vriend, E. Arnold, G. Kamer, M. G. Rossmann, M. A. McKinlay, G. D. Diana and M. J. Otto (1986). "The site of attachment in human rhinovirus 14 for antiviral agents that inhibit uncoating." Science 233: 1286-1293.

What is claimed is:

1. A method for immunizing a mammal against rhinovirus infection, which comprises providing to a mammal an effective amount of an immunogenic composition comprising one or more peptide, wherein the one or more peptide are selected from SEQ ID Nos. 1 or 2, or mixtures thereof.

2. The method of claim 1, wherein the rhinovirus infection is a human rhinovirus Group 1 virus.

3. The method of claim 2, wherein the peptide comprises SEQ ID No. 1.

4. The method of claim 3, wherein the peptide is coupled to a carrier molecule.

5. The method of claim 4, wherein the carrier molecule is selected from keyhole limpet hemocyanin, and BSA.

6. The method of claim 1, wherein the rhinovirus infection is a human rhinovirus Group 2 virus.

7. The method of claim 6, wherein the peptide comprises SEQ ID No. 2.

8. The method of claim 7, wherein the peptide is coupled to a carrier molecule.

9. The method of claim 8, wherein the carrier molecule is selected from keyhole limpet hemocyanin, and BSA.

10. The method of claim 1, wherein the rhinovirus is selected from human rhinovirus 14, human rhinovirus 16, and human rhinovirus 29.

* * * * *

SEQUENCE LISTING

```
<160> NUMBER OF SEQ ID NOS: 110

<210> SEQ ID NO 1
<211> LENGTH: 31
<212> TYPE: PRT
<213> ORGANISM: Artificial Sequence
<220> FEATURE:
<223> OTHER INFORMATION: Artificial Sequence - non-limiting example of
      peptide vaccine against Rhinoviruses.

<400> SEQUENCE: 1

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr
            20                  25                  30

<210> SEQ ID NO 2
<211> LENGTH: 24
<212> TYPE: PRT
<213> ORGANISM: Artificial Sequence
<220> FEATURE:
<223> OTHER INFORMATION: Artificial Sequence - non-limiting example of
      peptide vaccine against Rhinoviruses.

<400> SEQUENCE: 2

Gly Ala Gln Val Ser Arg Gln Asn Val Gly Thr His Ser Thr Gln Asn
1               5                   10                  15

Met Val Ser Asn Gly Ser Ser Leu
            20

<210> SEQ ID NO 3
<211> LENGTH: 50
<212> TYPE: PRT
<213> ORGANISM: Human rhinovirus

<400> SEQUENCE: 3

Gly Ala Gln Val Ser Thr Gln Lys Ser Gly Ser His Glu Asn Gln Asn
1               5                   10                  15

Ile Leu Thr Asn Gly Ser His Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
    50

<210> SEQ ID NO 4
<211> LENGTH: 50
<212> TYPE: PRT
<213> ORGANISM: Human rhinovirus

<400> SEQUENCE: 4

Gly Ala Gln Val Ser Thr Gln Lys Ser Gly Ser His Glu Asn Gln Asn
1               5                   10                  15
```

```
Ile Leu Thr Asn Gly Ser His Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
    50

<210> SEQ ID NO 5
<211> LENGTH: 50
<212> TYPE: PRT
<213> ORGANISM: Human rhinovirus

<400> SEQUENCE: 5

Gly Ala Gln Val Ser Thr Gln Lys Ser Gly Ser His Glu Asn Gln Asn
1               5                   10                  15

Ile Leu Thr Asn Gly Ser His Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
    50

<210> SEQ ID NO 6
<211> LENGTH: 50
<212> TYPE: PRT
<213> ORGANISM: Human rhinovirus

<400> SEQUENCE: 6

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
    50

<210> SEQ ID NO 7
<211> LENGTH: 50
<212> TYPE: PRT
<213> ORGANISM: Human rhinovirus

<400> SEQUENCE: 7

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
    50

<210> SEQ ID NO 8
<211> LENGTH: 50
<212> TYPE: PRT
<213> ORGANISM: Human rhinovirus

<400> SEQUENCE: 8

Gly Ala Gln Val Ser Thr Gln Lys Ser Gly Ser His Glu Asn Gln Asn
1               5                   10                  15
```

Phe Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
   50

<210> SEQ ID NO 9
<211> LENGTH: 50
<212> TYPE: PRT
<213> ORGANISM: Human rhinovirus

<400> SEQUENCE: 9

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
   50

<210> SEQ ID NO 10
<211> LENGTH: 50
<212> TYPE: PRT
<213> ORGANISM: Human rhinovirus

<400> SEQUENCE: 10

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
   50

<210> SEQ ID NO 11
<211> LENGTH: 50
<212> TYPE: PRT
<213> ORGANISM: Human rhinovirus

<400> SEQUENCE: 11

Gly Ala Gln Ile Ser Thr Gln Lys Ser Gly Ser His Glu Tyr Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
   50

<210> SEQ ID NO 12
<211> LENGTH: 50
<212> TYPE: PRT
<213> ORGANISM: Human rhinovirus

<400> SEQUENCE: 12

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 13
<211> LENGTH: 50
<212> TYPE: PRT
<213> ORGANISM: Human rhinovirus

<400> SEQUENCE: 13

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 14
<211> LENGTH: 50
<212> TYPE: PRT
<213> ORGANISM: Human rhinovirus

<400> SEQUENCE: 14

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 15
<211> LENGTH: 50
<212> TYPE: PRT
<213> ORGANISM: Human rhinovirus

<400> SEQUENCE: 15

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 16
<211> LENGTH: 50
<212> TYPE: PRT
<213> ORGANISM: Human rhinovirus

<400> SEQUENCE: 16

Gly Ala Gln Val Ser Thr Gln Lys Ser Gly Ser His Glu Asn Gln Asn
1               5                   10                  15

```
Ile Leu Thr Asn Gly Ser His Gln Thr Phe Thr Val Ile Asn Tyr Tyr
            20                  25                  30

Lys Asp Ala Ala Ser Ser Ser Ala Ser Gln Ser Phe Ser Met Asp
        35                  40                  45

Pro Ser
    50

<210> SEQ ID NO 17
<211> LENGTH: 50
<212> TYPE: PRT
<213> ORGANISM: Human rhinovirus

<400> SEQUENCE: 17

Gly Ala Gln Val Ser Thr Gln Lys Ser Gly Ser His Glu Asn Gln Asn
1               5                   10                  15

Ile Leu Thr Asn Gly Ser Asn Gln Thr Phe Thr Val Ile Asn Tyr Tyr
            20                  25                  30

Lys Asp Ala Ala Ser Ser Ser Ala Ser Gln Ser Phe Ser Met Asp
        35                  40                  45

Pro Ser
    50

<210> SEQ ID NO 18
<211> LENGTH: 50
<212> TYPE: PRT
<213> ORGANISM: Human rhinovirus

<400> SEQUENCE: 18

Gly Ala Gln Val Ser Thr Gln Arg Ser Gly Ser His Glu Asn Gln Asn
1               5                   10                  15

Ile Leu Thr Asn Gly Ser His Gln Thr Phe Thr Val Ile Asn Tyr Tyr
            20                  25                  30

Lys Asp Ala Ala Ser Ala Ser Ala Gly Gln Ser Phe Ser Met Asp
        35                  40                  45

Pro Ser
    50

<210> SEQ ID NO 19
<211> LENGTH: 50
<212> TYPE: PRT
<213> ORGANISM: Human rhinovirus

<400> SEQUENCE: 19

Gly Ala Gln Val Ser Thr Gln Lys Ser Gly Ser His Glu Asn Gln Asn
1               5                   10                  15

Phe Leu Ser Asn Gly Ser Asn Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
    50

<210> SEQ ID NO 20
<211> LENGTH: 50
<212> TYPE: PRT
<213> ORGANISM: Human rhinovirus

<400> SEQUENCE: 20

Gly Ala Gln Val Ser Thr Gln Lys Ser Gly Ser His Glu Ile Gln Asn
1               5                   10                  15
```

```
Met Leu Thr Asn Gly Ser His Gln Thr Phe Thr Val Ile Asn Tyr Tyr
            20                  25                  30

Lys Asp Ala Ala Ser Ser Ser Ala Gly Gln Ser Leu Ser Met Asp
        35                  40                  45

Pro Ser
    50

<210> SEQ ID NO 21
<211> LENGTH: 50
<212> TYPE: PRT
<213> ORGANISM: Human rhinovirus

<400> SEQUENCE: 21

Gly Ala Gln Val Ser Thr Gln Lys Ser Gly Ser His Glu Asn Gln Asn
1               5                   10                  15

Ile Leu Thr Asn Gly Ser Thr Gln His Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 22
<211> LENGTH: 50
<212> TYPE: PRT
<213> ORGANISM: Human rhinovirus

<400> SEQUENCE: 22

Gly Ala Gln Val Ser Thr Gln Lys Ser Gly Ser His Glu Asn Gln Asn
1               5                   10                  15

Ile Leu Thr Asn Gly Ser Thr Gln His Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 23
<211> LENGTH: 50
<212> TYPE: PRT
<213> ORGANISM: Human rhinovirus

<400> SEQUENCE: 23

Gly Ala Gln Val Ser Thr Gln Lys Ser Gly Ser His Glu Asn Gln Asn
1               5                   10                  15

Ile Leu Thr Asn Gly Ser Thr Gln His Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 24
<211> LENGTH: 50
<212> TYPE: PRT
<213> ORGANISM: Human rhinovirus

<400> SEQUENCE: 24

Gly Ala Gln Val Ser Thr Gln Lys Ser Gly Ser His Glu Asn Gln Thr
1               5                   10                  15
```

-continued

Ile Leu Thr Asn Gly Ser Thr Gln Pro Phe Thr Val Ile Asn Tyr Tyr
            20                  25                  30

Lys Asp Ala Ala Ser Ser Ser Ala Gly Gln Ser Phe Ser Met Asp
        35                  40                  45

Pro Ser
    50

<210> SEQ ID NO 25
<211> LENGTH: 50
<212> TYPE: PRT
<213> ORGANISM: Human rhinovirus

<400> SEQUENCE: 25

Gly Ala Gln Val Ser Thr Gln Lys Ser Gly Ser His Glu Asn Gln Asn
1               5                   10                  15

Ile Leu Thr Asn Gly Ser Thr Gln Asn Phe Thr Val Ile Asn Tyr Tyr
            20                  25                  30

Lys Asp Ala Ala Ser Ser Ser Ala Ser Gly Ser Phe Ser Met Asp
        35                  40                  45

Pro Ser
    50

<210> SEQ ID NO 26
<211> LENGTH: 50
<212> TYPE: PRT
<213> ORGANISM: Human rhinovirus

<400> SEQUENCE: 26

Gly Ala Gln Val Ser Thr Gln Lys Ser Gly Ser His Glu Asn Gln Asn
1               5                   10                  15

Ile Leu Thr Asn Gly Ser Thr His Thr Phe Thr Val Ile Asn Tyr Tyr
            20                  25                  30

Lys Asp Ala Ala Ser Ser Ser Ala Ser Gln Ser Phe Ser Met Asp
        35                  40                  45

Pro Ser
    50

<210> SEQ ID NO 27
<211> LENGTH: 50
<212> TYPE: PRT
<213> ORGANISM: Human rhinovirus

<400> SEQUENCE: 27

Gly Ala Gln Val Thr Arg Gln Gln Thr Gly Thr His Glu Asn Ala Asn
1               5                   10                  15

Ile Ala Thr Asn Gly Ser His Ile Thr Tyr Asn Gln Ile Asn Phe Tyr
            20                  25                  30

Lys Asp Ser Tyr Ala Ala Ser Ala Ser Lys Gln Asp Phe Ser Gln Asp
        35                  40                  45

Pro Ser
    50

<210> SEQ ID NO 28
<211> LENGTH: 50
<212> TYPE: PRT
<213> ORGANISM: Human rhinovirus

<400> SEQUENCE: 28

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 29
<211> LENGTH: 50
<212> TYPE: PRT
<213> ORGANISM: Human rhinovirus

<400> SEQUENCE: 29

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 30
<211> LENGTH: 50
<212> TYPE: PRT
<213> ORGANISM: Human rhinovirus

<400> SEQUENCE: 30

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 31
<211> LENGTH: 50
<212> TYPE: PRT
<213> ORGANISM: Human rhinovirus

<400> SEQUENCE: 31

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 32
<211> LENGTH: 50
<212> TYPE: PRT
<213> ORGANISM: Human rhinovirus

<400> SEQUENCE: 32

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 33
<211> LENGTH: 50
<212> TYPE: PRT
<213> ORGANISM: Human rhinovirus

<400> SEQUENCE: 33

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 34
<211> LENGTH: 50
<212> TYPE: PRT
<213> ORGANISM: Human rhinovirus

<400> SEQUENCE: 34

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 35
<211> LENGTH: 50
<212> TYPE: PRT
<213> ORGANISM: Human rhinovirus

<400> SEQUENCE: 35

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 36
<211> LENGTH: 50
<212> TYPE: PRT
<213> ORGANISM: Human rhinovirus

<400> SEQUENCE: 36

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 37
<211> LENGTH: 50
<212> TYPE: PRT
<213> ORGANISM: Human rhinovirus

<400> SEQUENCE: 37

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 38
<211> LENGTH: 50
<212> TYPE: PRT
<213> ORGANISM: Human rhinovirus

<400> SEQUENCE: 38

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 39
<211> LENGTH: 50
<212> TYPE: PRT
<213> ORGANISM: Human rhinovirus

<400> SEQUENCE: 39

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 40
<211> LENGTH: 50
<212> TYPE: PRT
<213> ORGANISM: Human rhinovirus

<400> SEQUENCE: 40

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 41
<211> LENGTH: 50
<212> TYPE: PRT
<213> ORGANISM: Human rhinovirus

<400> SEQUENCE: 41

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 42
<211> LENGTH: 50
<212> TYPE: PRT
<213> ORGANISM: Human rhinovirus

<400> SEQUENCE: 42

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 43
<211> LENGTH: 50
<212> TYPE: PRT
<213> ORGANISM: Human rhinovirus

<400> SEQUENCE: 43

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
   50

<210> SEQ ID NO 44
<211> LENGTH: 50
<212> TYPE: PRT
<213> ORGANISM: Human rhinovirus

<400> SEQUENCE: 44

Gly Ala Gln Val Ser Arg Gln Asn Val Gly Thr His Ser Thr Gln Asn
1               5                   10                  15

-continued

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 45
<211> LENGTH: 50
<212> TYPE: PRT
<213> ORGANISM: Human rhinovirus

<400> SEQUENCE: 45

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 46
<211> LENGTH: 50
<212> TYPE: PRT
<213> ORGANISM: Human rhinovirus

<400> SEQUENCE: 46

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 47
<211> LENGTH: 50
<212> TYPE: PRT
<213> ORGANISM: Human rhinovirus

<400> SEQUENCE: 47

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 48
<211> LENGTH: 50
<212> TYPE: PRT
<213> ORGANISM: Human rhinovirus

<400> SEQUENCE: 48

Gly Ala Gln Val Ser Arg Gln Asn Val Gly Thr His Ser Thr Gln Asn
1               5                   10                  15

```
Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 49
<211> LENGTH: 50
<212> TYPE: PRT
<213> ORGANISM: Human rhinovirus

<400> SEQUENCE: 49

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 50
<211> LENGTH: 50
<212> TYPE: PRT
<213> ORGANISM: Human rhinovirus

<400> SEQUENCE: 50

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 51
<211> LENGTH: 50
<212> TYPE: PRT
<213> ORGANISM: Human rhinovirus

<400> SEQUENCE: 51

Gly Thr Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 52
<211> LENGTH: 50
<212> TYPE: PRT
<213> ORGANISM: Human rhinovirus

<400> SEQUENCE: 52

Gly Ala Gln Val Ser Arg Gln Asn Val Gly Thr His Ser Thr Gln Asn
1               5                   10                  15
```

Ser Gly Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 53
<211> LENGTH: 50
<212> TYPE: PRT
<213> ORGANISM: Human rhinovirus

<400> SEQUENCE: 53

Gly Ala Gln Val Ser Arg Gln Asn Val Gly Thr His Ser Thr Gln Asn
1               5                   10                  15

Ser Val Thr Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 54
<211> LENGTH: 50
<212> TYPE: PRT
<213> ORGANISM: Human rhinovirus

<400> SEQUENCE: 54

Gly Ala Gln Val Ser Arg Gln Asn Val Gly Thr His Ser Thr Gln Asn
1               5                   10                  15

Ser Val Thr Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 55
<211> LENGTH: 50
<212> TYPE: PRT
<213> ORGANISM: Human rhinovirus

<400> SEQUENCE: 55

Gly Ala Gln Val Ser Arg Gln Asn Val Gly Thr His Ser Thr Gln Asn
1               5                   10                  15

Ser Val Thr Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 56
<211> LENGTH: 50
<212> TYPE: PRT
<213> ORGANISM: Human rhinovirus

<400> SEQUENCE: 56

Gly Ala Gln Val Ser Arg Gln Asn Val Gly Thr His Ser Thr Gln Asn
1               5                   10                  15

Ser Val Ser Gly Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 57
<211> LENGTH: 50
<212> TYPE: PRT
<213> ORGANISM: Human rhinovirus

<400> SEQUENCE: 57

Gly Ala Gln Val Ser Arg Gln Asn Val Gly Thr His Ser Thr Gln Asn
1               5                   10                  15

Ser Val Ser His Gly Ser Ser Leu Asn Tyr Phe Asn Ile His Tyr Phe
            20                  25                  30

Lys Asp Ala Ala Ser Ser Gly Ala Phe Lys Leu Glu Phe Ser Gln Asp
        35                  40                  45

Pro Ser
    50

<210> SEQ ID NO 58
<211> LENGTH: 50
<212> TYPE: PRT
<213> ORGANISM: Human rhinovirus

<400> SEQUENCE: 58

Gly Ala Gln Val Ser Arg Gln Asn Val Gly Thr His Ser Thr Gln Asn
1               5                   10                  15

Val Val Ser Ser Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 59
<211> LENGTH: 50
<212> TYPE: PRT
<213> ORGANISM: Human rhinovirus

<400> SEQUENCE: 59

Gly Ala Gln Val Ser Arg Gln Asn Val Gly Thr His Ser Thr Gln Asn
1               5                   10                  15

Ser Val Ser Asn Gly Ser Ser Leu Asn Phe Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 60
<211> LENGTH: 50
<212> TYPE: PRT
<213> ORGANISM: Human rhinovirus

<400> SEQUENCE: 60

Gly Ala Gln Val Ser Arg Gln Asn Val Gly Thr His Ser Thr Gln Asn
1               5                   10                  15

Thr Val Ser Asn Gly Ser Ser Leu Asn Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 61
<211> LENGTH: 50
<212> TYPE: PRT
<213> ORGANISM: Human rhinovirus

<400> SEQUENCE: 61

Gly Ala Gln Val Ser Arg Gln Asn Val Gly Thr His Ser Thr Gln Asn
1               5                   10                  15

Thr Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 62
<211> LENGTH: 50
<212> TYPE: PRT
<213> ORGANISM: Human rhinovirus

<400> SEQUENCE: 62

Gly Ala Gln Val Ser Arg Gln Asn Val Gly Thr His Ser Thr Gln Asn
1               5                   10                  15

Thr Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 63
<211> LENGTH: 50
<212> TYPE: PRT
<213> ORGANISM: Human rhinovirus

<400> SEQUENCE: 63

Gly Ala Gln Val Ser Arg Gln Asn Val Gly Thr His Ser Thr Gln Asn
1               5                   10                  15

Thr Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 64
<211> LENGTH: 50
<212> TYPE: PRT
<213> ORGANISM: Human rhinovirus

<400> SEQUENCE: 64

Gly Ala Gln Val Ser Arg Gln Asn Val Gly Thr His Ser Thr Gln Asn
1               5                   10                  15

Ala Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 65
<211> LENGTH: 50
<212> TYPE: PRT
<213> ORGANISM: Human rhinovirus

<400> SEQUENCE: 65

Gly Ala Gln Val Ser Arg Gln Asn Val Gly Thr His Ser Thr Gln Asn
1               5                   10                  15

Ala Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 66
<211> LENGTH: 50
<212> TYPE: PRT
<213> ORGANISM: Human rhinovirus

<400> SEQUENCE: 66

Gly Ala Gln Val Ser Arg Gln Asn Val Gly Thr His Ser Thr Gln Asn
1               5                   10                  15

Ala Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 67
<211> LENGTH: 50
<212> TYPE: PRT
<213> ORGANISM: Human rhinovirus

<400> SEQUENCE: 67

Gly Ala Gln Val Ser Arg Gln Asn Val Gly Thr His Ser Thr Gln Asn
1               5                   10                  15

Ala Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 68
<211> LENGTH: 50
<212> TYPE: PRT
<213> ORGANISM: Human rhinovirus

<400> SEQUENCE: 68

Gly Ala Gln Val Ser Arg Gln Asn Val Gly Thr His Ser Thr Gln Asn
1               5                   10                  15

Ala Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 69
<211> LENGTH: 50
<212> TYPE: PRT
<213> ORGANISM: Human rhinovirus

<400> SEQUENCE: 69

Gly Ala Gln Val Ser Arg Gln Asn Val Gly Thr His Ser Thr Gln Asn
1               5                   10                  15

Met Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 70
<211> LENGTH: 50
<212> TYPE: PRT
<213> ORGANISM: Human rhinovirus

<400> SEQUENCE: 70

Gly Ala Gln Val Ser Arg Gln Asn Val Gly Thr His Ser Thr Gln Asn
1               5                   10                  15

Met Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 71
<211> LENGTH: 50
<212> TYPE: PRT
<213> ORGANISM: Human rhinovirus

<400> SEQUENCE: 71

Gly Ala Gln Val Ser Arg Gln Asn Val Gly Thr His Ser Thr Gln Asn
1               5                   10                  15

Met Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser
    50

<210> SEQ ID NO 72
<211> LENGTH: 50
<212> TYPE: PRT
<213> ORGANISM: Human rhinovirus

<400> SEQUENCE: 72

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Asn Gly Ala Ser Lys Leu Asp Phe Thr Gln Asp
        35                  40                  45

Pro Ser
    50

<210> SEQ ID NO 73
<211> LENGTH: 50
<212> TYPE: PRT
<213> ORGANISM: Human rhinovirus

<400> SEQUENCE: 73

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Asn Gly Ala Ser Lys Leu Glu Phe Thr Gln Asp
        35                  40                  45

Pro Ser
    50

<210> SEQ ID NO 74
<211> LENGTH: 50
<212> TYPE: PRT
<213> ORGANISM: Human rhinovirus

<400> SEQUENCE: 74

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Asn Gly Ala Ser Lys Leu Glu Phe Ser Gln Asp
        35                  40                  45

Pro Ser
    50

<210> SEQ ID NO 75
<211> LENGTH: 50
<212> TYPE: PRT
<213> ORGANISM: Human rhinovirus

<400> SEQUENCE: 75

Gly Ala Gln Val Ser Arg Gln Asn Val Gly Thr His Ser Thr Gln Asn
1               5                   10                  15

Ala Val Thr Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 76
<211> LENGTH: 50
<212> TYPE: PRT
<213> ORGANISM: Human rhinovirus

<400> SEQUENCE: 76

Gly Ala Gln Val Ser Arg Gln Asn Val Gly Thr His Ser Thr Gln Asn
1               5                   10                  15

```
Ala Val Thr Asn Gly Ser Arg Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 77
<211> LENGTH: 50
<212> TYPE: PRT
<213> ORGANISM: Human rhinovirus

<400> SEQUENCE: 77

Gly Ala Gln Val Ser Arg Gln Asn Val Gly Thr His Ser Thr Gln Asn
1               5                   10                  15

Ala Val Ser Gly Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 78
<211> LENGTH: 50
<212> TYPE: PRT
<213> ORGANISM: Human rhinovirus

<400> SEQUENCE: 78

Gly Ala Gln Val Ser Arg Gln Asn Val Gly Thr His Ser Thr Gln Asn
1               5                   10                  15

Ala Val Ser Gly Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 79
<211> LENGTH: 50
<212> TYPE: PRT
<213> ORGANISM: Human rhinovirus

<400> SEQUENCE: 79

Gly Ala Gln Val Ser Arg Gln Asn Val Gly Thr His Ser Thr Gln Asn
1               5                   10                  15

Thr Val Thr Gly Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 80
<211> LENGTH: 50
<212> TYPE: PRT
<213> ORGANISM: Human rhinovirus

<400> SEQUENCE: 80

Gly Ala Gln Val Ser Arg Gln Asn Val Gly Thr His Thr Thr Gln Asn
1               5                   10                  15
```

```
Ala Val Ser Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 81
<211> LENGTH: 50
<212> TYPE: PRT
<213> ORGANISM: Human rhinovirus

<400> SEQUENCE: 81

Gly Ala Gln Val Ser Arg Gln Asn Val Gly Thr His Ser Thr Gln Asn
1               5                   10                  15

Thr Val Ala Asn Gly Ser Ser Leu Asn Tyr Phe Asn Ile Asn Tyr Phe
            20                  25                  30

Lys Asp Ala Ala Ser Asn Gly Ala Ser Arg Leu Asp Phe Ser Gln Asp
        35                  40                  45

Pro Ser
    50

<210> SEQ ID NO 82
<211> LENGTH: 50
<212> TYPE: PRT
<213> ORGANISM: Human rhinovirus

<400> SEQUENCE: 82

Gly Ala Gln Val Ser Arg Gln Asn Val Gly Thr His Ser Thr Gln Asn
1               5                   10                  15

Thr Val Ala Asn Gly Ser Ser Leu Asn Tyr Phe Asn Ile Asn Tyr Phe
            20                  25                  30

Lys Asp Ala Ala Ser Asn Gly Ala Ser Arg Leu Asp Phe Ser Gln Asp
        35                  40                  45

Pro Ser
    50

<210> SEQ ID NO 83
<211> LENGTH: 50
<212> TYPE: PRT
<213> ORGANISM: Human rhinovirus

<400> SEQUENCE: 83

Gly Ala Gln Val Ser Arg Gln Asn Val Gly Thr His Ser Thr Gln Asn
1               5                   10                  15

Thr Val Ala Asn Gly Ser Ser Leu Asn Tyr Phe Asn Ile Asn Tyr Phe
            20                  25                  30

Lys Asp Ala Ala Ser Asn Gly Ala Ser Arg Leu Asp Phe Ser Gln Asp
        35                  40                  45

Pro Ser
    50

<210> SEQ ID NO 84
<211> LENGTH: 50
<212> TYPE: PRT
<213> ORGANISM: Human rhinovirus

<400> SEQUENCE: 84

Gly Ala Gln Val Ser Arg Gln Asn Val Gly Thr His Ser Thr Gln Asn
1               5                   10                  15
```

Thr Val Ala Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 85
<211> LENGTH: 49
<212> TYPE: PRT
<213> ORGANISM: Human rhinovirus

<400> SEQUENCE: 85

Gly Ala Gln Val Ser Arg Gln Asn Val Thr His Ser Thr Gln Asn Ala
1               5                   10                  15

Val Ser Asn Gly Ser Ser Leu Asn Tyr Phe Asn Ile Asn Tyr Phe Lys
            20                  25                  30

Asp Ala Ala Ser Ser Gly Ala Ser Arg Leu Asp Phe Ser Gln Asp Pro
        35                  40                  45

Ser

<210> SEQ ID NO 86
<211> LENGTH: 50
<212> TYPE: PRT
<213> ORGANISM: Human rhinovirus

<400> SEQUENCE: 86

Gly Ala Gln Val Ser Arg Gln Asn Val Gly Thr His Ser Thr Gln Asn
1               5                   10                  15

Ala Val Ser Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 87
<211> LENGTH: 50
<212> TYPE: PRT
<213> ORGANISM: Human rhinovirus

<400> SEQUENCE: 87

Gly Ala Gln Val Ser Arg Gln Asn Val Gly Thr His Ser Thr Gln Asn
1               5                   10                  15

Ala Val Thr Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 88
<211> LENGTH: 50
<212> TYPE: PRT
<213> ORGANISM: Human rhinovirus

<400> SEQUENCE: 88

Gly Ala Gln Val Ser Arg Gln Asn Val Gly Thr His Ser Thr Gln Asn
1               5                   10                  15

Ala Val Thr Asn Gly Ser Ser Leu Asn Tyr Phe Asn Ile Asn Tyr Phe

```
                    20                  25                  30
Lys Asp Ala Ala Ser Ser Gly Ala Ser Arg Leu Asp Phe Ser Gln Asp
        35                  40                  45

Pro Ser
    50

<210> SEQ ID NO 89
<211> LENGTH: 50
<212> TYPE: PRT
<213> ORGANISM: Human rhinovirus

<400> SEQUENCE: 89

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
                20                  25                  30

Lys Asp Ala Ala Ser Ser Gly Ala Ser Arg Leu Asp Phe Ser Gln Asp
        35                  40                  45

Pro Ser
    50

<210> SEQ ID NO 90
<211> LENGTH: 50
<212> TYPE: PRT
<213> ORGANISM: Human rhinovirus

<400> SEQUENCE: 90

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
                20                  25                  30

Lys Asp Ala Ala Ser Ser Gly Ala Ser Arg Leu Asp Phe Ser Gln Asp
        35                  40                  45

Pro Ser
    50

<210> SEQ ID NO 91
<211> LENGTH: 50
<212> TYPE: PRT
<213> ORGANISM: Human rhinovirus

<400> SEQUENCE: 91

Gly Ala Gln Val Ser Arg Gln Asn Val Gly Thr His Ser Thr Gln Asn
1               5                   10                  15

Met Val Ser Asn Gly Ser Ser Leu Asn Tyr Phe Asn Ile Asn Tyr Phe
                20                  25                  30

Lys Asp Ala Ala Ser Ser Gly Ala Ser Arg Leu Asp Phe Ser Gln Asp
        35                  40                  45

Pro Ser
    50

<210> SEQ ID NO 92
<211> LENGTH: 50
<212> TYPE: PRT
<213> ORGANISM: Human rhinovirus

<400> SEQUENCE: 92

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
```

-continued

```
                    20                  25                  30
Lys Asp Ala Ala Ser Ser Gly Ala Ser Arg Leu Asp Phe Ser Gln Asp
        35                  40                  45

Pro Ser
    50

<210> SEQ ID NO 93
<211> LENGTH: 50
<212> TYPE: PRT
<213> ORGANISM: Human rhinovirus

<400> SEQUENCE: 93

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 94
<211> LENGTH: 50
<212> TYPE: PRT
<213> ORGANISM: Human rhinovirus

<400> SEQUENCE: 94

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 95
<211> LENGTH: 50
<212> TYPE: PRT
<213> ORGANISM: Human rhinovirus

<400> SEQUENCE: 95

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser
    50

<210> SEQ ID NO 96
<211> LENGTH: 50
<212> TYPE: PRT
<213> ORGANISM: Human rhinovirus

<400> SEQUENCE: 96

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
```

```
                    20                  25                  30

Lys Asp Ala Ala Ser His Gly Ala Ser Lys Leu Asp Phe Ser Gln Asp
        35                  40                  45

Pro Ser
    50

<210> SEQ ID NO 97
<211> LENGTH: 50
<212> TYPE: PRT
<213> ORGANISM: Human rhinovirus

<400> SEQUENCE: 97

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser His Gly Ala Ser Lys Leu Asp Phe Ser Gln Asp
        35                  40                  45

Pro Ser
    50

<210> SEQ ID NO 98
<211> LENGTH: 50
<212> TYPE: PRT
<213> ORGANISM: Human rhinovirus

<400> SEQUENCE: 98

Gly Ala Gln Val Ser Arg Gln Asn Val Gly Thr His Ser Thr Gln Asn
1               5                   10                  15

Thr Val Ser Asn Gly Ser Ser Leu Asn Tyr Phe Asn Ile Asn Tyr Phe
            20                  25                  30

Lys Asp Ala Ala Ser His Gly Ala Ser Lys Leu Asp Phe Ser Gln Asp
        35                  40                  45

Pro Ser
    50

<210> SEQ ID NO 99
<211> LENGTH: 50
<212> TYPE: PRT
<213> ORGANISM: Human rhinovirus

<400> SEQUENCE: 99

Gly Ala Gln Val Ser Asn Gln Asn Val Gly Thr His Ser Thr Gln Asn
1               5                   10                  15

Pro Val Ser Asn Gly Ser Ser Leu Asn Tyr Phe Lys Ile Asn Tyr Phe
            20                  25                  30

Lys Asp Ala Ala Ser Asn Gly Ala Ser Lys Leu Glu Phe Ser Gln Asp
        35                  40                  45

Pro Ser
    50

<210> SEQ ID NO 100
<211> LENGTH: 90
<212> TYPE: DNA
<213> ORGANISM: Human rhinovirus

<400> SEQUENCE: 100
ggcgctcagg tttctacaca gaaaagtgga tctcacgaaa atcaaaacat tttgaccaat      60
ggatcaaatc agactttcac agttataaat                                      90
```

<210> SEQ ID NO 101
<211> LENGTH: 72
<212> TYPE: DNA
<213> ORGANISM: Human rhinovirus

<400> SEQUENCE: 101
ggcgctcaag tatctagaca gaatgttggt acgcactcaa cacaaaatat ggtgtcaaat    60
ggatccagcc tc                                                        72

<210> SEQ ID NO 102
<211> LENGTH: 15
<212> TYPE: PRT
<213> ORGANISM: Human rhinovirus

<400> SEQUENCE: 102

Gly Ala Gln Val Ser Thr Gln Lys Ser Gly Ser His Glu Asn Gln
1               5                   10                  15

<210> SEQ ID NO 103
<211> LENGTH: 15
<212> TYPE: PRT
<213> ORGANISM: Human rhinovirus

<400> SEQUENCE: 103

Gly Ala Gln Val Ser Arg Gln Asn Val Gly Thr His Ser Thr Gln
1               5                   10                  15

<210> SEQ ID NO 104
<211> LENGTH: 15
<212> TYPE: PRT
<213> ORGANISM: Human rhinovirus

<400> SEQUENCE: 104

Gly Ala Gln Val Ser Arg Gln Asn Val Gly Thr His Ser Thr Gln
1               5                   10                  15

<210> SEQ ID NO 105
<211> LENGTH: 15
<212> TYPE: PRT
<213> ORGANISM: Human rhinovirus

<400> SEQUENCE: 105

Gly Ala Gln Val Ser Arg Gln Asn Val Gly Thr His Ser Thr Gln
1               5                   10                  15

<210> SEQ ID NO 106
<211> LENGTH: 15
<212> TYPE: PRT
<213> ORGANISM: Human rhinovirus

<400> SEQUENCE: 106

Gly Ala Gln Val Ser Arg Gln Asn Val Gly Thr His Ser Thr Gln
1               5                   10                  15

<210> SEQ ID NO 107
<211> LENGTH: 15
<212> TYPE: PRT
<213> ORGANISM: Human rhinovirus

<400> SEQUENCE: 107

Gly Ala Gln Val Ser Arg Gln Asn Val Gly Thr His Ser Thr Gln
1               5                   10                  15

<210> SEQ ID NO 108

```
<211> LENGTH: 15
<212> TYPE: PRT
<213> ORGANISM: Human rhinovirus

<400> SEQUENCE: 108

Gly Ala Gln Val Ser Arg Gln Asn Val Gly Thr His Ser Thr Gln
1               5                   10                  15

<210> SEQ ID NO 109
<211> LENGTH: 15
<212> TYPE: PRT
<213> ORGANISM: Human rhinovirus

<400> SEQUENCE: 109

Gly Ala Gln Val Ser Arg Gln Asn Val Gly Thr His Ser Thr Gln
1               5                   10                  15

<210> SEQ ID NO 110
<211> LENGTH: 15
<212> TYPE: PRT
<213> ORGANISM: Human rhinovirus

<400> SEQUENCE: 110

Gly Ala Gln Val Ser Arg Gln Asn Val Gly Thr His Ser Thr Gln
1               5                   10                  15
```